US010974223B2

(12) United States Patent
Shuto et al.

(10) Patent No.: US 10,974,223 B2
(45) Date of Patent: Apr. 13, 2021

(54) METHOD FOR PRODUCING WATER ABSORBENT RESIN

(71) Applicant: NIPPON SHOKUBAI CO., LTD., Osaka (JP)

(72) Inventors: Tokio Shuto, Suita (JP); Motohiro Imura, Himeji (JP); Shin-Ichi Fujino, Himeji (JP); Koji Honda, Himeji (JP); Ryota Wakabayashi, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 16/066,509

(22) PCT Filed: Dec. 28, 2016

(86) PCT No.: PCT/JP2016/089156
§ 371 (c)(1),
(2) Date: Jun. 27, 2018

(87) PCT Pub. No.: WO2017/115861
PCT Pub. Date: Jul. 6, 2017

(65) Prior Publication Data
US 2019/0001302 A1    Jan. 3, 2019

(30) Foreign Application Priority Data
Dec. 28, 2015   (JP) ............................. JP2015-256603

(51) Int. Cl.
*A61L 15/60*          (2006.01)
*B01J 19/06*          (2006.01)
(Continued)

(52) U.S. Cl.
CPC ............. *B01J 20/267* (2013.01); *A61L 15/24* (2013.01); *A61L 15/60* (2013.01); *B01J 19/06* (2013.01);
(Continued)

(58) Field of Classification Search
CPC . B01D 11/02; B01D 11/0261; B01D 11/0269; B01D 11/0273; B01D 11/0276;
(Continued)

(56) References Cited

U.S. PATENT DOCUMENTS 3,234,303 A * 2/1966 Bild ...................... C08F 291/02
525/52
3,579,728 A * 5/1971 Reid .................... B01J 19/0006
425/86
(Continued)

FOREIGN PATENT DOCUMENTS

CN      202862630 U  *  4/2013
EP        0789047 A1     8/1997
(Continued)

OTHER PUBLICATIONS

English machine translation of Su et al. (CN 202862630 U). (Year: 2013).*

(Continued)

*Primary Examiner* — Matthew R Diaz
(74) *Attorney, Agent, or Firm* — Dickinson Wright PLLC

(57) ABSTRACT

[Object] To provide a method for producing a water-absorbent resin in powder form or particle form, which has excellent physical properties such as water absorption performance and the like, at high productivity.
[Solution] A method for producing a water-absorbent resin includes: a polymerization step of polymerizing a monomer, which is a raw material of the water-absorbent resin, to obtain a hydrous gel crosslinked polymer dispersed in an organic solvent; and a separation step of separating the organic solvent and the hydrous gel crosslinked polymer. The separation step includes transfer, compression, and discharge of the hydrous gel crosslinked polymer.

12 Claims, 11 Drawing Sheets

(51) Int. Cl.
  *B01J 20/26* (2006.01)
  *B01J 20/28* (2006.01)
  *B01J 20/30* (2006.01)
  *C08J 3/075* (2006.01)
  *C08F 6/00* (2006.01)
  *A61L 15/24* (2006.01)
  *C08F 220/06* (2006.01)

(52) U.S. Cl.
  CPC ....... *B01J 20/261* (2013.01); *B01J 20/28011* (2013.01); *B01J 20/28047* (2013.01); *B01J 20/3007* (2013.01); *B01J 20/3035* (2013.01); *B01J 20/3085* (2013.01); *C08F 6/008* (2013.01); *C08F 220/06* (2013.01); *C08J 3/075* (2013.01); *B01J 2220/68* (2013.01); *C08F 2810/20* (2013.01); *C08G 2210/00* (2013.01)

(58) Field of Classification Search
  CPC ....... B01J 8/10; B01J 8/20; B01J 20/26; B01J 20/261; B01J 20/265; B01J 20/267; B01J 20/28011; B01J 20/28047; B01J 20/30; B01J 20/3007; B01J 20/3035; B01J 20/3085; B01J 2220/68; B01J 19/06; C08F 2/32; C08F 6/008; C08F 6/10; C08F 6/20; C08F 6/24; C08F 220/06; C08F 2810/20; C08J 3/075; C08J 3/091; C08J 3/092; C08G 2210/00; A61L 15/24; A61L 15/60
  USPC ....................................................... 252/194
  See application file for complete search history.

(56) References Cited

U.S. PATENT DOCUMENTS

| | | | |
|---|---|---|---|
| 4,340,706 A | 7/1982 | Obayashi et al. | |
| 4,459,396 A * | 7/1984 | Yamasaki | C08F 2/32 526/200 |
| 4,683,274 A | 7/1987 | Nakamura et al. | |
| 5,180,798 A | 1/1993 | Nakamura et al. | |
| 6,140,395 A * | 10/2000 | Hatsuda | B29B 7/186 523/319 |
| 6,949,622 B2 * | 9/2005 | Silvi | C08G 63/89 528/481 |
| 7,322,738 B2 * | 1/2008 | Yamane | B29C 48/52 366/75 |
| 7,638,570 B2 | 12/2009 | Torii et al. | |
| 2006/0168841 A1 * | 8/2006 | Kouno | B01F 7/088 34/179 |
| 2018/0071714 A1 | 3/2018 | Torii et al. | |

FOREIGN PATENT DOCUMENTS

| | | |
|---|---|---|
| JP | H08-085709 A | 4/1996 |
| JP | H11-071425 A | 3/1999 |
| JP | H11-080248 A | 3/1999 |
| JP | 2001-002713 A | 1/2001 |
| JP | 2001-002726 A | 1/2001 |
| JP | 2001200062 A | 7/2001 |
| JP | 2004-269593 A | 9/2004 |
| JP | 2012012482 A | 1/2012 |
| WO | WO 2006/014031 A1 | 2/2006 |
| WO | WO 2016/159144 A1 | 10/2016 |

OTHER PUBLICATIONS

Modern Superabsorbent Polymer Technology, Chapter 3, 1998, edited by Fredric L. Buchholz and Andrew T. Graham, Wiley-VCH.
International Search Report dated Feb. 24, 2017 in corresponding Patent Application No. PCT/JP2016/089156, including Eng. Translation.

* cited by examiner

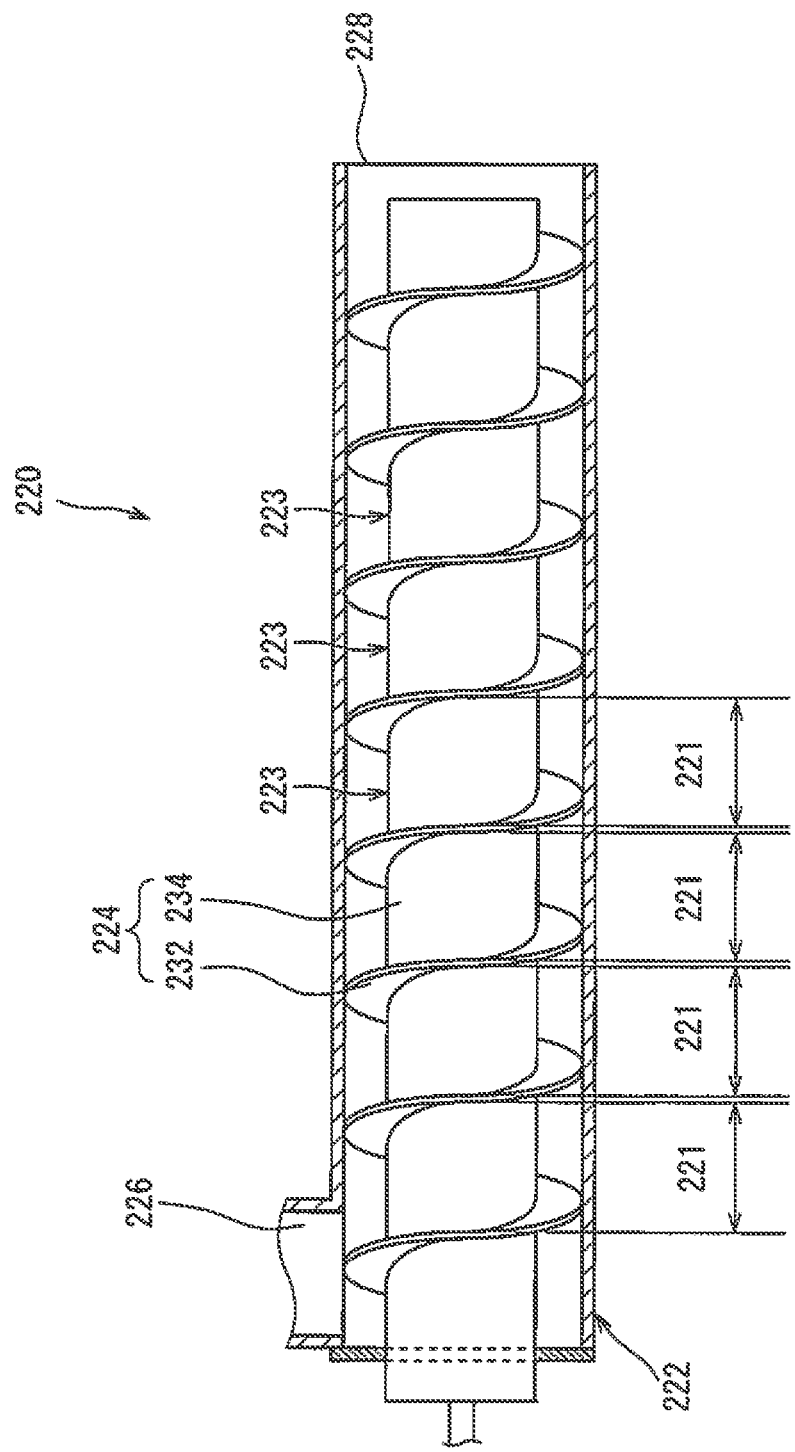

METHOD FOR PRODUCING WATER ABSORBENT RESIN

TECHNICAL FIELD

The present invention relates to methods for producing a water-absorbent resin. More specifically, the present invention relates to methods for producing a water-absorbent resin in which a hydrous gel crosslinked polymer obtained by polymerization is efficiently extracted from a polymerization device and separated from an organic solvent.

BACKGROUND ART

A water-absorbent resin is a water-swellable and water-insoluble crosslinked polymer that absorbs a large amount of an aqueous liquid and gelates, and a common form thereof is particle form. Methods for industrially producing the water-absorbent resin are generally classified into two types, aqueous solution polymerization in which water is used as a solvent, and reverse phase suspension polymerization in which an organic solvent is used as a dispersion medium (Non-Patent Literature 1).

In the reverse phase suspension polymerization, a large amount of an organic solvent is required in order to disperse droplets of a monomer aqueous solution. Therefore, separation of the organic solvent and a hydrous gel crosslinked polymer obtained by polymerization is troublesome, so that there was a disadvantage in terms of cost and there were also problems about odor and safety due to the organic solvent remaining in the water-absorbent resin. Accordingly, as means for separating the organic solvent, a method of evaporating an organic solvent in dispersant of a water-absorbent resin or a hydrous gel thereof, whereby the water-absorbent resin or the hydrous gel thereof is isolated (dried) (Patent Literature 1 to 3), and a method in which a water-absorbent resin or a hydrous gel thereof is filtered out from an organic solvent, have been known.

Specifically, as the above filtration method, separation by decantation, a thickener, or the like has been known, but removal of the solvent by such a method is not sufficient. Therefore, as a solid-liquid separator, a gravity filtration type, a vacuum filtration type, a pressure filtration type, a centrifugal filtration type, and a centrifugal sedimentation type have been proposed (Patent Literature 4 and 5). In addition, a separation method using a centrifuge has been proposed (Patent Literature 6).

Furthermore, in the reverse phase suspension polymerization, an expensive surfactant and a dispersing agent are generally used in order to disperse the monomer aqueous solution. As described above, in the conventional reverse phase suspension polymerization, separation between the hydrous gel crosslinked polymer and the organic solvent is troublesome, and the same applies to the surfactant and the dispersing agent. Therefore, there is a disadvantage in terms of cost and there are also problems such as a decrease in surface tension and a decrease in water absorption speed due to the surfactant or the dispersing agent remaining in the water-absorbent resin. Accordingly, a technique to wash away the surfactant from the water-absorbent resin obtained by the reverse phase suspension polymerization (Patent Literature 7 and 8) has been proposed. However, the cost for washing is large, and recovery of the surfactant is also insufficient.

In addition, a solution for the odor problem caused by the remaining organic solvent (Patent Literature 9) has also been proposed, but this solution adds a new step and thus is disadvantageous in terms of cost.

CITATION LIST

Patent Literature

Patent Literature 1: U.S. Pat. No. 4,340,706
Patent Literature 2: U.S. Pat. No. 4,683,274
Patent Literature 3: U.S. Pat. No. 5,180,798
Patent Literature 4: JP2001-2713
Patent Literature 5: JP2001-2726
Patent Literature 6: JP8-85709
Patent Literature 7: JP11-080248
Patent Literature 8: JP11-071425
Patent Literature 9: WO2006/014031

Non Patent Literature

Non-Patent Literature 1: Modern Superabsorbent Polymer Technology, Third Chapter (1998)

SUMMARY OF THE INVENTION

Problems to be Solved by the Invention

As described above, in the conventional reverse phase suspension polymerization, evaporation to dryness and filtration are adopted for separation of the used organic solvent and the water-absorbent resin, but these separation techniques are inefficient. In the conventional filtration device as described above, it is necessary to filter the entire amount including the organic solvent, which is inefficient. Furthermore, a decrease in filtration efficiency due to clogging of a filter medium is also observed. Thus, in order to improve the filtration efficiency, it is necessary to quantitatively extract a slurry from a transfer device and supply the slurry to a continuous filtration device. However, in particular, in the case where a reaction device is large in size, the liquid surface of the organic solvent is high with respect to a discharge port, and thus the liquid pressure (back pressure) increases to make it difficult to extract the slurry, so that a further large-scale control device is required. In the case with the above decantation or thickener, it is not necessary to filter the entire amount of the organic solvent, and thus the above decantation or thickener is efficient. However, a problem arises in that removal of the organic solvent is insufficient, or due to influence of an increase in liquid pressure (back pressure) caused by size increase of the reaction device, the organic solvent also flows out together when the settled hydrous gel is extracted. In any of the cases, it is difficult to extract the hydrous gel from the large-sized reaction device and sufficiently remove the organic solvent by evaporation to dryness or filtration, which is a conventional technique. Furthermore, the organic solvent or the surfactant remaining in the water-absorbent resin has an adverse effect not only in terms of odor and safety but also in terms of cost and physical properties.

Therefore, the present inventors have conducted thorough research for a new solid-liquid separation method in a process for separating a hydrous gel crosslinked polymer and an organic solvent from each other, and have found a new method that enables more efficient separation.

An object of the present invention is to efficiently produce a water-absorbent resin, particularly, spherical or substantially spherical water-absorbent resin particles.

Solution to the Problems

As a result of thorough research for achieving the above object, the present inventors have completed the following invention. Specifically, a method for producing a water-absorbent resin according to the present invention is a method for producing a water-absorbent resin including: a polymerization step of polymerizing a monomer, which is a raw material of the water-absorbent resin, to obtain a hydrous gel crosslinked polymer dispersed in an organic solvent; and a separation step of separating the organic solvent and the hydrous gel crosslinked polymer from each other, wherein the separation step includes transfer, compression, and discharge of the hydrous gel crosslinked polymer.

Advantageous Effects of the Invention

With the method for producing the water-absorbent resin according to the present invention, in the separation step of separating the hydrous gel crosslinked polymer and the organic solvent from each other, the hydrous gel crosslinked polymer is efficiently squeezed by using the discharge device capable of transferring and discharging the hydrous gel crosslinked polymer, so that high production efficiency and a low residual liquid ratio are simultaneously achieved. In addition, by decreasing the residual liquid ratio, it is possible to achieve simplification of a drying step or reduction in the amount of the organic solvent remaining in the water-absorbent resin. As a result, a water-absorbent resin reduced in odor due to the organic solvent is obtained. Furthermore, since the surfactant and/or the dispersing agent remaining in the water-absorbent resin is also reduced, a water-absorbent resin having high surface tension is obtained. Moreover, problems such as clogging in conventional separation by filtration, remaining the entire amount of the used surfactant or dispersing agent in the water-absorbent resin and high energy required for evaporation of a solvent in conventional separation by evaporation to dryness, do not occur.

BRIEF DESCRIPTION OF THE DRAWINGS

FIG. 11 is a schematic diagram showing a discharge device in which the inner diameter of a casing and the diameter of a shaft portion are uniform, a pitch is uniform, and no pressure adjustment mechanism is present at a discharge port.

DESCRIPTION OF EMBODIMENTS

Figure 1:
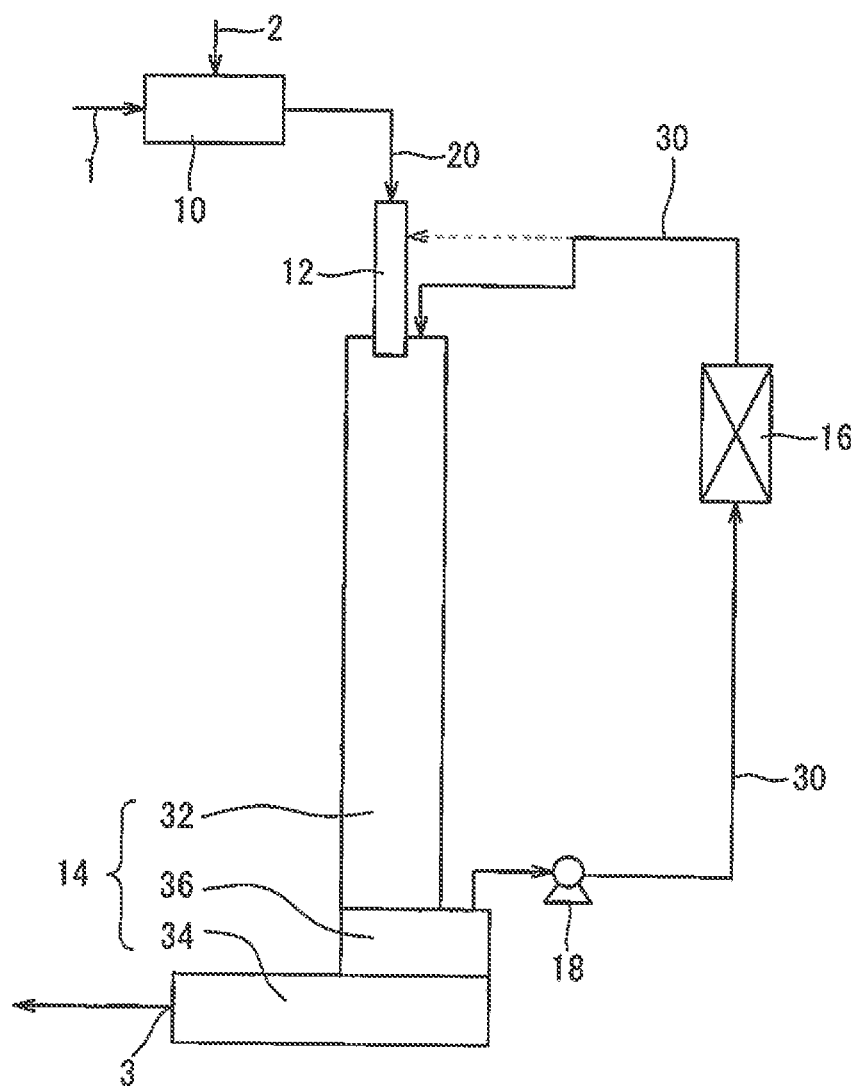
FIG. 1 is a schematic diagram showing a part of a process for producing a water-absorbent resin according to an embodiment of the present invention.

The following will describe in detail the present invention. However, the scope of the present invention is not limited to the following description, and the present invention may be carried out by making modifications as appropriate without impairing the gist of the present invention, in addition to the following examples. Moreover, the present invention is not limited to the following embodiments, and various modifications may be made within the scope indicated by the claims. Another embodiment achieved by combining, as appropriate, each technical means disclosed in a plurality of embodiments is also included within the technical scope of the present invention.

[1] Definition of Terms

[1-1] "Water-Absorbent Resin"

The term "water-absorbent resin" in the present invention refers to a water-swellable and water-insoluble polymer gelling agent that satisfies the following physical properties. That is, "water-absorbent resin" refers to a polymer gelling agent whose CRC (centrifuge retention capacity) defined by ERT441.2-02 as water swellability is not less than 5 g/g and whose Ext (water-soluble content) defined by ERT470.2-02 as water insolubility is not greater than 50% by mass.

The water-absorbent resin can be designed in accordance with the application and/or purpose thereof, and is preferably a hydrophilic crosslinked polymer obtained by crosslinking and polymerizing an unsaturated monomer having a carboxyl group. In addition, the water-absorbent resin is not limited to a resin entirely composed of a crosslinked polymer, and may be a composition containing an additive and the like as long as each of the above physical properties (CRC, Ext) satisfies the above numerical range.

"Water-absorbent resin" in the present invention is not limited to a final product before shipment, and may refer to an intermediate in the production process for a water-absorbent resin (e.g., a hydrous gel crosslinked polymer after polymerization, water-absorbent resin powder before surface-crosslinking, etc.). All of them are collectively referred to as "water-absorbent resin".

[1-2] "Polyacrylic Acid (Salt)"

The term "polyacrylic acid (salt)" in the present invention refers to a polyacrylic acid and/or a salt thereof, and means a crosslinked polymer that contains a repeating unit of acrylic acid and/or a salt thereof (hereinafter referred to as "acrylic acid (salt)") as a main component and that contains a graft component as an optional component.

The term "main component" means that the used amount (contained amount) of the acrylic acid (salt) with respect to the entire monomer to be used in polymerization is preferably 50% by mole to 100% by mole, more preferably 70% by mole to 100% by mole, further preferably 90% by mole to 100% by mole, and particularly preferably substantially 100% by mole.

The term "polyacrylic acid salt" as a crosslinked polymer includes a water-soluble salt of polyacrylic acid, and includes preferably a monovalent salt, more preferably an alkali metal salt or ammonium salt, further preferably an alkali metal salt, particularly preferably a sodium salt.

[1-3] "EDANA" and "ERT"

The term "EDANA" is an abbreviation for the European Disposables and Nonwovens Associations, and the term "ERT" is an abbreviation for EDANA Recommended Test Methods, which are European standard measuring methods for water-absorbent resin. In the present invention, unless otherwise specified, physical properties of the water-absorbent resin are measured according to the ERT original text (revised in 2002).

(a) "CRC" (ERT441.2-02)

The term "CRC" is an abbreviation for Centrifuge Retention Capacity, and means the fluid retention capacity without pressure (sometimes referred to as "fluid retention capacity") of the water-absorbent resin. Specifically, CRC refers to a fluid retention capacity (unit: g/g) measured after 0.2 g of the water-absorbent resin put in a nonwoven fabric is immersed in a large excess of a 0.9% by mass sodium chloride aqueous solution for 30 minutes to be freely swollen and then drained in a centrifuge (250 G) for 3 minutes.

(b) "AAP" (ERT442.2-02)

The term "AAP" is an abbreviation for Absorption Against Pressure, and means the fluid retention capacity under load of the water-absorbent resin. Specifically, AAP refers to a fluid retention capacity (unit: g/g) measured after 0.9 g of the water-absorbent resin is swollen in a large excess of a 0.9% by mass sodium chloride aqueous solution for 1 hour under a load of 2.06 kPa (21 g/cm$^2$, 0.3 psi). The fluid retention capacity may be measured with the load condition changed to 4.83 kPa (49 g/cm$^2$, 0.7 psi). Although "Absorption Under Pressure" is described in ERT442.2-02, AAP is substantially the same as "Absorption Under Pressure".

(c) "Ext" (ERT470.2-02)

The term "Ext" is an abbreviation for Extractables, and means the water-soluble component content (water-soluble component amount) of the water-absorbent resin. Specifically, Ext refers to the amount (unit: % by mass) of substances dissolved in 200 ml of a 0.9% by mass sodium chloride aqueous solution after 1.0 g of the water-absorbent resin is added to the aqueous solution and the aqueous solution is stirred at 500 rpm for 16 hours. For measuring the water-soluble content, pH titration is used.

(d) "Residual Monomers" (ERT410.2-02)

The term "Residual Monomers" means the amount of the monomer remaining in the water-absorbent resin. Hereinafter, the monomer remaining in the water-absorbent resin is referred to as "residual monomer". Specifically, the amount of the monomer refers to the amount (unit: ppm) of the monomer dissolved in 200 ml of a 0.9% by mass sodium chloride aqueous solution after 1.0 g of the water-absorbent resin is added to the aqueous solution and the aqueous solution is stirred at 500 rpm for 1 hour. For measuring the amount of the residual monomer, high-performance liquid chromatography (HPLC) is used.

(e) "Moisture Content" (ERT430.2-02)

The term "Moisture Content" means the moisture content of the water-absorbent resin. Specifically, the moisture content refers to a value (unit: % by mass) calculated from a drying loss when 4.0 g of the water-absorbent resin is dried at 105° C. for 3 hours. The moisture content may be measured with the amount of the water-absorbent resin changed to 1.0 g and with the drying temperature changed to 180° C.

(f) "PSD" (ERT420.2-02)

The term "PSD" is an abbreviation for Particle Size Distribution, which means the particle size distribution of the water-absorbent resin measured by sieve classification. A mass-average particle diameter (D50) and the logarithmic standard deviation ($\sigma\zeta$) of the particle size distribution are measured by the same methods as in "(3) Mass-Average Particle Diameter (D50) and Logarithmic Standard Deviation ($\sigma\zeta$) of Particle Diameter Distribution" described in U.S. Pat. No. 7,638,570.

[1-4] Others

In the present specification, "X to Y" indicating a range means "not less than X and not greater than Y". Unless otherwise noted, the mass unit "t (ton)" refers to "metric ton", and "ppm" refers to "ppm by mass" or "ppm by weight". Furthermore, "mass" and "weight", "part(s) by mass" and "part(s) by weight", and "% by mass" and "% by weight" are synonymous with each other. Moreover, " . . . acid (salt)" means " . . . acid and/or a salt thereof", and "(meth)acrylic" means "acrylic and/or methacrylic".

[2] Method for Producing Water-Absorbent Resin

The method for producing the water-absorbent resin according to the present invention includes: a mixing step of mixing a monomer aqueous solution, which contains a monomer that is a raw material of the water-absorbent resin, with a polymerization initiator to prepare a monomer composition; a supplying step of supplying the monomer composition to a reactor in which an organic solvent is stored; a polymerization step of initiating a polymerization reaction in the reactor to obtain a hydrous gel crosslinked polymer; a separation step of separating the hydrous gel crosslinked polymer from the organic solvent; and other post-steps.

The following will describe each step (the mixing step, the supplying step, the polymerization step, the separation step, and the other post-steps) in detail.

[2-1] Mixing Step

This step is a step of mixing an aqueous solution that contains, as a main component, a later-described monomer that is a raw material of the water-absorbent resin (hereinafter, referred to as "monomer aqueous solution"), with a polymerization initiator to prepare a monomer composition. In the present specification, for the sake of convenience, the "monomer aqueous solution" and the "monomer composition" are distinguished from each other on the basis of presence/absence of a polymerization initiator. That is, a monomer aqueous solution containing a polymerization initiator is referred to as "monomer composition".

(Monomer)

In the method for producing the water-absorbent resin according to the present invention, the monomer to be used only needs to be a compound that can be polymerized into a water-absorbent resin. Examples of the monomer include: acid group-containing unsaturated monomers such as (meth)acrylic acid, maleic acid (anhydride), itaconic acid, cinnamic acid, vinylsulfonic acid, allyltoluene sulfonic acid, vinyltoluene sulfonic acid, styrene sulfonic acid, 2-(meth)acrylamide-2-methylpropane sulfonic acid, 2-(meth)acryloylethane sulfonic acid, 2-(meth)acryloylpropane sulfonic acid, and 2-hydroxyethyl(meth)acryloyl phosphate; amide group-containing unsaturated monomers such as (meth)

acrylamide, N-ethyl(meth)acrylamide, and N,N-dimethyl (meth)acrylamide; amino group-containing unsaturated monomers such as N,N-dimethylaminoethyl(meth)acrylate, N,N-dimethylaminopropyl(meth)acrylate, and N,N-dimethylaminopropyl(meth)acrylamide; mercapto group-containing unsaturated monomers; phenolic hydroxyl group-containing unsaturated monomers; lactam group-containing unsaturated monomers such as N-vinylpyrrolidone; and the like.

Among the above monomers, when an acid group-containing unsaturated monomer having an acid group such as a carboxyl group is used, the monomer is preferably a partially neutralized salt obtained by neutralizing a part of the acid group, from the viewpoint of the water absorption performance of the obtained water-absorbent resin. In this case, the salt is preferably at least one monovalent salt selected from an alkali metal salt, an ammonium salt, and an amine salt, more preferably an alkali metal salt, further preferably at least one salt selected from a sodium salt, a lithium salt, and a potassium salt, and particularly preferably a sodium salt.

Among them, from the viewpoint of the water absorption performance of the obtained water-absorbent resin, the monomer is a preferably an acid group-containing unsaturated monomer and/or a salt thereof, more preferably (meth)acrylic acid (salt), maleic acid (anhydride) (salt), itaconic acid (salt), or cinnamic acid (salt), and further preferably acrylic acid (salt).

In the method according to the present invention, when an acid group-containing unsaturated monomer is used as the monomer, a neutralized salt of the acid group-containing unsaturated monomer is preferably used in combination from the viewpoint of the water absorption performance of the obtained water-absorbent resin. In addition, from the viewpoint of the water absorption performance of the obtained water-absorbent resin, the number of moles of the neutralized salt relative to the total number of moles of the acid group-containing unsaturated monomer and the neutralized salt thereof (hereinafter, referred to as "neutralization ratio") is preferably not less than 40% by mole, more preferably 40% by mole to 80% by mole, further preferably 45% by mole to 78% by mole, and particularly preferably 50% by mole to 75% by mole, with respect to the acid group of the acid group-containing unsaturated monomer. Unless otherwise specified, the concept of the monomer in the present invention includes a neutralized salt thereof.

Examples of the method for adjusting the neutralization ratio include: a method in which the acid group-containing unsaturated monomer and the neutralized salt thereof are mixed with each other; a method in which a known neutralizer is added to the acid group-containing unsaturated monomer; a method in which a partially neutralized salt of the acid group-containing unsaturated monomer that is adjusted in advance to a predetermined neutralization ratio (i.e., a mixture of the acid group-containing unsaturated monomer and the neutralized salt thereof) is used; and the like. In addition, these methods can be combined as appropriate.

Examples of the neutralizer to be used for neutralizing the acid group-containing unsaturated monomer include inorganic salts such as sodium hydroxide, potassium hydroxide, sodium carbonate, and ammonium carbonate, and basic substances such as an amine-based organic compound having an amino group or an imino group. Two or more of these neutralizers can be used in combination as appropriate.

The adjustment of the neutralization ratio may be performed before initiation of a polymerization reaction of the acid group-containing unsaturated monomer, may be performed during a polymerization reaction of the acid group-containing unsaturated monomer, or may be performed on a hydrous gel crosslinked polymer obtained after end of the polymerization reaction of the acid group-containing unsaturated monomer. In addition, the neutralization ratio may be adjusted at any one stage selected from among: before initiation of the polymerization reaction; during the polymerization reaction; and after end of the polymerization reaction, or the neutralization ratio may be adjusted at a plurality of stages among them. In application to absorbent articles such as disposable diapers and the like in which there is a possibility of direct contact with a human body, the neutralization ratio is adjusted preferably before initiation of the polymerization reaction and/or during the polymerization reaction, and more preferably before initiation of the polymerization reaction.

In the method according to the present invention, any of the monomers described above as examples may be used solely, or any two or more of the monomers may be mixed as appropriate and used. In addition, another monomer may be further mixed as long as the object of the present invention is achieved.

When two or more of the monomers are used in combination, acrylic acid (salt) is preferably contained as a main component. In this case, from the viewpoint of the water absorption performance of the obtained water-absorbent resin, the proportion of the acrylic acid (salt) to the entire monomer is normally not less than 50% by mole, preferably not less than 70% by mole, more preferably not less than 80% by mole, and further preferably not less than 90% by mole. The upper limit thereof is 100% by mole.

(Internal Crosslinking Agent)

In the method for producing the water-absorbent resin according to the present invention, an internal crosslinking agent is preferably used. By the internal crosslinking agent, the water absorption performance of the obtained water-absorbent resin, the gel strength thereof at the time of water absorption, and the like are adjusted.

The internal crosslinking agent only needs to have two or more unsaturated bonds or reactive functional groups within one molecule thereof. Examples of the internal crosslinking agent include N,N-methylene bis(meth)acrylamide, (poly)ethylene glycol di(meth)acrylate, (poly)propylene glycol di(meth)acrylate, trimethylol propane tri(meth)acrylate, glycerin (meth)acrylate, glycerin acrylate methacrylate, ethylene oxide-modified trimethylol propane tri(meth)acrylate, pentaerythritol hexa(meth)acrylate, triallyl cyanurate, triallyl isocyanurate, triallyl phosphate, triallylamine, polyallyloxy alkane, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, glycidyl (meth)acrylate, and the like. Two or more of them may be used in combination.

The used amount of the internal crosslinking agent is set as appropriate in accordance with the types of the monomer and the internal crosslinking agent and the like. Specifically, from the viewpoint of the gel strength of the obtained water-absorbent resin, the used amount of the internal crosslinking agent with respect to the monomer is preferably not less than 0.001% by mole, more preferably not less than 0.005% by mole, and further preferably not less than 0.01% by mole. In addition, from the viewpoint of improvement of the water absorption performance of the water-absorbent resin, the used amount of the internal crosslinking agent is preferably not greater than 5% by mole and more preferably not greater than 2% by mole. In a polymerization condition in which a self-crosslinking reaction of the monomer is effective, the internal crosslinking agent may not be used.

(Additive)

In the method for producing the water-absorbent resin according to the present invention, a substance (hereinafter, referred to as "additive") whose examples will be described below can be added.

Specific examples of the additive include: chain transfer agents such as thiols, thiolic acids, secondary alcohols, amines, and hypophosphites; foaming agents such as carbonates, bicarbonates, azo compounds, and bubbles; chelating agents such as metal salts of ethylenediamine tetraacetic acid, and metal salts of diethylenetriamine pentaacetic acid; hydrophilic polymers such as polyacrylic acid (salt) and crosslinked products thereof, starch, cellulose, starch-cellulose derivatives, and polyvinyl alcohol; and the like. These additives may be used solely, or two or more of these additives may be used in combination.

The used amount of the additives is preferably not greater than 10% by mass as the concentration of all the additives in the monomer aqueous solution.

(Polymerization Initiator)

As the polymerization initiator to be used in the method for producing the water-absorbent resin according to the present invention, a pyrolytic polymerization initiator is preferably used. The pyrolytic polymerization initiator refers to a compound that is decomposed by heat to generate radicals. From the viewpoint of storage stability and production efficiency, a water-soluble compound having a 10-hour half-life temperature (hereinafter, referred to as "T10") of preferably 0° C. to 120° C., more preferably 30° C. to 100° C., and further preferably 50° C. to 80° C. is used as the pyrolytic polymerization initiator.

Specific examples of the pyrolytic polymerization initiator include: persulfates such as sodium persulfate, potassium persulfate, and ammonium persulfate; azo compounds such as 2,2'-azobis(2-methylpropionamidine)dihydrochloride, 2,2'-azobis(2-amidinopropane)dihydrochloride, 2,2'-azobis[2-(2-imidazoline-2-yl)propane]dihydrochloride, and 2,2'-azobis(2-methylpropionitrile); peroxides such as hydrogen peroxide, t-butyl peroxide, and methyl ethyl ketone peroxide; and the like. Two or more of them may be used in combination.

Among them, from the viewpoint of the handleability of the pyrolytic polymerization initiator and the physical properties of the water-absorbent resin, persulfates are preferably used, sodium persulfate, potassium persulfate, and ammonium persulfate are more preferably used, and sodium persulfate is further preferably used.

The used amount of the pyrolytic polymerization initiator is set as appropriate in accordance with the types of the monomer and the polymerization initiator and the like. Specifically, from the viewpoint of production efficiency, the used amount of the pyrolytic polymerization initiator with respect to the monomer is preferably not less than 0.001 g/mol, more preferably not less than 0.005 g/mol, and further preferably not less than 0.01 g/mol. In addition, from the viewpoint of improvement of the water absorption performance of the water-absorbent resin, the used amount of the pyrolytic polymerization initiator is preferably not greater than 2 g/mol and more preferably not greater than 1 g/mol.

In addition, as necessary, the pyrolytic polymerization initiator can be used in combination with another polymerization initiator such as a photolytic polymerization initiator. Specific examples of the photolytic polymerization initiator include benzoin derivatives, benzyl derivatives, acetophenone derivatives, benzophenone derivatives, and the like.

When the pyrolytic polymerization initiator and another polymerization initiator are used in combination, the proportion of the pyrolytic polymerization initiator to the entire polymerization initiator is preferably not less than 60% by mole and more preferably not less than 80% by mole.

In addition, the pyrolytic polymerization initiator and a reducing agent can be used in combination as a redox polymerization initiator. In the redox polymerization initiator, the pyrolytic polymerization initiator serves as an oxidizing agent. Examples of the reducing agent to be used include: (bi)sulfites such as sodium sulfite and sodium hydrogen sulfite; reducing metal salts such as ferrous salts; L-ascorbic acid (salt); amines; and the like.

(Method for Preparing Monomer Composition)

In this process, a monomer composition containing the monomer aqueous solution and the polymerization initiator is prepared. Examples of the method for preparing the monomer composition include (1) a method in which a monomer aqueous solution and an aqueous solution containing the polymerization initiator (hereinafter, referred to as "polymerization initiator aqueous solution") are prepared in advance, are supplied simultaneously to a mixing device through different pipes, and are mixed therein; (2) a method in which a monomer aqueous solution that is prepared in advance is supplied to a mixing device, and then the polymerization initiator is supplied to the mixing device and mixed therewith; (3) a method in which a monomer aqueous solution that is prepared in advance is supplied to the mixing device, and then an polymerization initiator aqueous solution that is prepared in advance is supplied to the mixing device and mixed therewith; and the like.

Examples of the above mixing device include a line mixer, a tank, and the like. From the viewpoint of the storage stability of the polymerization initiator and the safety, the above method (1) for mixing, in which a line mixer is used as the mixing device, is preferable.

A method in which the above monomer aqueous solution and the above polymerization initiator (including the polymerization initiator aqueous solution) are supplied directly to the reactor using different pipes, not via a supply device, can also be adopted. That is, in this case, a monomer composition is not prepared, and the monomer aqueous solution and the polymerization initiator (including the polymerization initiator aqueous solution) are individually supplied to the reactor.

(Concentration of Monomer Component)

In this step, in preparing the monomer composition, the above respective substances are mixed. The monomer in the monomer composition is referred to as "monomer component". Specifically, from the viewpoint of the physical properties and the productivity of the water-absorbent resin, the concentration of the monomer component in the monomer composition is preferably 10% by mass to 90% by mass, more preferably 20% by mass to 80% by mass, and further preferably 30% by mass to 70% by mass. Hereinafter, the concentration of the monomer component is sometimes referred to as "monomer concentration".

The "concentration of the monomer component" is obtained by the following (formula 1). In (formula 1), Mc (unit: % by mass) is the "concentration of the monomer component", M1 (unit: kg) is the "mass of the monomer", and M2 (unit: kg) is the "mass of the monomer composition". The mass M2 of the monomer composition does not include the masses of a graft component, the water-absorbent resin, an organic solvent described later, and the like.

$$Mc=(M1/M2)\times 100 \qquad \text{(formula 1)}$$

(Temperature of Monomer Composition)

The temperature (hereinafter, referred to as "Tm") of the monomer composition obtained by the above series of operations is preferably kept at a temperature lower than the 10-hour half-life temperature T10 of the pyrolytic polymerization initiator contained in the monomer composition, until the monomer composition is put into the organic solvent in the reactor.

From the viewpoint of the storage stability of the monomer composition and avoidance of production trouble, the difference ΔT1 (=T10−Tm) between the temperature Tm and the temperature T10 is preferably not lower than 10° C., more preferably not lower than 15° C., and further preferably not lower than 20° C. The upper limit thereof is preferably 50° C. from the viewpoint of cost.

(Dissolved Oxygen Amount of Monomer Composition)

In the monomer composition, the amount of oxygen dissolved is preferably reduced prior to polymerization, in order to promote the polymerization reaction. The amount of oxygen dissolved therein is preferably not greater than 10 ppm, more preferably not greater than 5 ppm, further preferably not greater than 3 ppm, and particularly preferably not greater than 1 ppm. Examples of the method for reducing oxygen dissolved in the monomer composition include a method in which a raw material having a small amount of oxygen dissolved therein is used, a method in which inert gas such as nitrogen is introduced, temperature rise by heating the monomer aqueous solution or the monomer composition, and the like.

[2-2] Supplying Step

This step is a step of supplying the monomer composition obtained in the above mixing step to the reactor.

(Supply Device)

The monomer composition obtained in the above mixing step is supplied via a supply device to the reactor in which the organic solvent is stored. In the case where the polymerization step described below is batchwise, the organic solvent and the monomer composition only need to be supplied in predetermined amounts, and the supply device is not particularly limited. For example, a pipe and the like are used as the supply device. Meanwhile, in the case where the polymerization step described below is continuous, a supply device capable of supplying the monomer composition in the form of droplets is preferable.

As the supply device, for example, a device can be used in which a liquid column or a liquid film of the monomer composition is discharged from one or two or more orifices or nozzles, and is broken up in the organic solvent or vapor phase to generate droplets. Specifically, examples of the supply device include: cylindrical nozzles such as needles; an orifice plate having multiple holes in a plate; one-fluid sprays such as a swirl injection valve, a fine spray nozzle, and a collision type injection valve; two-fluid sprays; multiple-fluid sprays for three or more fluids; centrifugal atomizers such as a rotary wheel; and the like. By using the supply device, the monomer composition is put into the organic solvent or the vapor phase.

From the viewpoint of the stability of a dispersion state or a suspension state of the droplets and the heat transfer efficiency of the organic solvent, the volume average particle diameter of the droplets formed in the above operation is preferably not greater than 2000 μm, more preferably not greater than 1000 μm, and further preferably not greater than 800 μm. In addition, from the viewpoint of production efficiency, the volume average particle diameter of the droplets formed is preferably not less than 1 μm, more preferably not less than 10 μm, and further preferably not less than 50 μm.

The "volume average particle diameter" of the droplets is measured by a method for calculation according to "Particle size analysis-Laser diffraction methods" specified in JIS Z 8825 or "Representation of results of particle size analysis—Part 2: Calculation of average particle sizes/diameters and moments from particle size distributions" specified in JIS Z 8819-2, by a method for calculation by image analysis of a picture obtained by photographing a dispersion state, or by other methods.

(Retention Time)

From the viewpoint of avoidance of production trouble such as a blockage of a pipe, the time until the monomer composition prepared in the above mixing step is put into the reactor (hereinafter, referred to as "retention time") is preferably not longer than 20 minutes, more preferably not longer than 5 minutes, and further preferably not longer than 1 minute. Ideally, the monomer composition is put into the reactor immediately after the monomer composition is prepared.

(Input Method)

In the case where the above polymerization method is continuous, the organic solvent in the reactor is preferably circulated. In this case, the monomer composition is preferably put inside so as to flow parallel to the direction in which the organic solvent is circulated. From this viewpoint, the angle formed by the direction in which the monomer composition is put inside and the direction in which the organic solvent is circulated is preferably not greater than 90 degrees, more preferably not greater than 70 degrees, further preferably not greater than 50 degrees, and particularly preferably not greater than 30 degrees. Ideally, the direction in which the monomer composition is put inside and the direction in which the organic solvent is circulated are parallel to each other. For example, when the monomer composition is sprayed in a conical shape by using the supply device, the direction in which the monomer composition is put inside means the direction of the central axis of the cone. In the case where the above polymerization method is batchwise, the monomer composition is put into the organic solvent that is left at rest or is being stirred, and thus the above angle is not used.

[2-3] Polymerization Step

This step is a step of polymerizing the monomer composition supplied to the reactor by the above supplying step, to obtain a hydrous gel crosslinked polymer (hereinafter, also referred to as "hydrous gel"). The hydrous gel obtained by the polymerization is in the form of particles dispersed in the organic solvent.

The polymerization in the present invention may be liquid-phase polymerization in which the monomer composition is dispersed into the organic solvent and polymerized, or may be vapor-phase polymerization in which the monomer composition is dispersed into the vapor phase and polymerized. Even in the case of vapor-phase polymerization, a hydrous gel obtained finally may be dispersed in the organic solvent. For example, in a mode in which a hydrous gel obtained by vapor-phase polymerization drops into the organic solvent, the hydrous gel is dispersed in the organic solvent, and thus it is necessary to separate the hydrous gel from the organic solvent. Thus, the present invention can also be applied to this case.

As in the above liquid-phase polymerization, polymerization and dispersion may simultaneously progress. Meanwhile, as in the above mode of vapor-phase polymerization, dispersion may be performed after polymerization.

(Organic Solvent)

The organic solvent to be used in the method for producing the water-absorbent resin according to the present invention refers to an organic compound that does not mutually dissolve with the monomer composition, that is, has low compatibility with the monomer composition and that is essentially hydrophobic. In addition, the organic solvent is essentially inactive against a polymerization reaction of the monomer that is the raw material of the water-absorbent resin of the present invention. The organic solvent is used as a dispersion medium.

Examples of the organic solvent (dispersion medium) in the present invention include a hydrophilic organic solvent, a hydrophobic organic solvent, or a mixed solvent thereof. A hydrophobic organic solvent is preferably used as a main component. The term "main component" means that the amount thereof with respect to the entire organic solvent is preferably not less than 50% by mass, more preferably not less than 90% by mass, and further preferably not less than 98% by mass. The term "hydrophobic organic solvent" refers to an organic solvent whose solubility in 100 g of water at 25° C. under normal pressure is preferably not greater than 1 g and more preferably not greater than 0.1 g.

Specific examples of the organic solvent include: aliphatic hydrocarbons such as n-pentane, n-hexane, n-heptane, and n-octane; alicyclic hydrocarbons such as cyclohexane, methylcyclohexane, cyclooctane, and decalin; aromatic hydrocarbons such as benzene, toluene, and xylene; halogenated hydrocarbons such as chlorobenzene, bromobenzene, carbon tetrachloride, and 1,2-dichloroethane; and the like. From the viewpoint of easy availability and quality stability of the organic solvent and the like, n-hexane, n-heptane, and cyclohexane are preferably used.

(Specific Gravity Adjuster)

In the method for producing the water-absorbent resin according to the present invention, a specific gravity adjuster is preferably blended in the organic solvent. By the specific gravity adjuster, the polymerization time in this step can be adjusted.

The specific gravity adjuster may be any adjuster as long as the adjuster has high compatibility with the organic solvent and does not inhibit the polymerization reaction. Examples of the specific gravity adjuster include chlorine-based or fluorine-based compounds such as hydrofluorocarbon, hydrofluoroether, hydrochlorofluorocarbon, and fluorides of alcohols, and the like. Two or more of them may be used in combination. Hereinafter, an organic solvent blended with these compounds as a specific gravity adjuster is sometimes referred to as "mixed solvent". Unless otherwise specified, the concept of the organic solvent in the present invention also includes a mixed solvent blended with the above specific gravity adjuster.

The used amount of the specific gravity adjuster is set as appropriate in accordance with the type of the organic solvent and the like such that a later-described specific gravity difference between the organic solvent and the monomer composition is achieved.

(Dispersing Agent)

In the method for producing the water-absorbent resin according to the present invention, a dispersing agent whose examples will be described below can be added to the above organic solvent. Preferable examples of the dispersing agent include a surfactant and a polymeric dispersing agent.

Specific examples of the surfactant include sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkylallylformaldehyde-condensed polyoxyethylene ethers, polyoxyethylene polyoxypropylene block copolymers, polyoxyethylene polyoxypropyl alkyl ethers, polyethylene glycol fatty acid esters, alkyl glucosides, N-alkyl gluconamides, polyoxyethylene fatty acid amides, polyoxyethylene alkylamines, phosphoric esters of polyoxyethylene alkyl ethers, phosphoric esters of polyoxyethylene alkyl aryl ethers, and the like. Two or more of them may be used in combination.

Specific examples of the polymeric dispersing agent include maleic anhydride-modified polyethylene, maleic anhydride-modified polypropylene, maleic anhydride-modified ethylene-propylene copolymer, maleic anhydride-modified ethylene-propylene-diene terpolymer (EPDM), maleic anhydride-modified polybutadiene, maleic anhydride-ethylene copolymer, maleic anhydride-propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylic acid copolymer, ethyl cellulose, ethyl hydroxyethyl cellulose, and the like. Among them, from the viewpoint of the dispersion stability of the monomer composition, maleic anhydride-modified polyethylene, maleic anhydride-modified polypropylene, maleic anhydride-modified ethylene-propylene copolymer, maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and oxidized ethylene-propylene copolymer are preferable. Two or more of them may be used in combination. In addition, these polymeric dispersing agents may be used in combination with the above surfactant.

The used amount of the dispersing agent is set as appropriate in accordance with the polymerization form, the types of the monomer composition and the organic solvent, and the like. Specifically, the concentration of the dispersing agent in the organic solvent is preferably not greater than 1.0% by mass, more preferably not greater than 0.5% by mass, and further preferably not greater than 0.1% by mass. In the present invention, the dispersing agent is not essential, but when the dispersing agent is used, the lower limit is preferably greater than 0% by mass and more preferably not less than 0.0001% by mass.

In the method according to the present invention, the organic solvent contains the above surfactant and/or polymeric dispersing agent. In such a case, the surfactant and/or polymeric dispersing agent contained in the organic solvent separated in the separation step is reused together with the organic solvent as it is.

(W/O Ratio)

In the present invention, the used amount of the organic solvent is set as appropriate in accordance with the shape and the capacity of the reactor and the like. From the viewpoint of removal of the heat of the polymerization reaction and production efficiency, the ratio of the volume W of the monomer composition to the volume O of the organic solvent in the reactor (hereinafter, referred to as "W/O ratio") is preferably 1% by volume to 40% by volume, more preferably 2% by volume to 30% by volume, and further preferably 3% by volume to 20% by volume.

The W/O ratio exceeding 40% by volume brings that removal of heat of polymerization is insufficient, the performance of the obtained water-absorbent resin deteriorates, and operation trouble such as bumping and poor formation of droplets easily occurs, therefore that is not preferable. On the other hand, the W/O ratio less than 1% by volume brings an increase in the used amount of the organic solvent or an increase in the size of the reactor, following that the cost increases in terms of material and facility, therefore that is not preferable. Unless otherwise specified, the volumes of the monomer composition and the organic solvent are volumes at 25° C. under 1 atmospheric pressure.

(Polymerization Temperature)

In the method according to the present invention, the temperature (hereinafter, referred to as "Td") of the organic solvent in the reactor is referred to as "polymerization temperature".

When the monomer composition is dispersed in the form of droplets into the organic solvent at a predetermined temperature, or when the monomer composition is dispersed in the form of droplets into the organic solvent and then heated to a predetermined temperature, the temperature of the monomer composition immediately rises to the temperature of the organic solvent or higher due to heat transfer from the organic solvent or heat of polymerization. The pyrolytic polymerization initiator contained in the droplets decomposes to generate radical with the temperature rise. The generated radical initiates a polymerization reaction, and a hydrous gel is formed with progress of the polymerization reaction. In the case of continuous polymerization, the formed hydrous gel moves within the reactor due to the circulated organic solvent, and is discharged from the reactor together with the organic solvent. The reactor has a product discharge port. The hydrous gel is discharged through the product discharge port. In addition, in the case of batchwise polymerization, after the polymerization reaction ends, the hydrous gel is discharged from the reactor together with the organic solvent.

From the viewpoint of a polymerization ratio, the polymerization temperature Td is preferably not lower than 70° C., more preferably not lower than 75° C., and further preferably not lower than 80° C. From the viewpoint of safety, the upper limit of the polymerization temperature Td is selected as appropriate from the range that does not exceed the boiling point of the used organic solvent.

When the polymerization temperature Td is less than 70° C., the polymerization speed decreases, and the polymerization ratio of the obtained hydrous gel may decrease or the particle diameter of the obtained hydrous gel may be greatly varied. Furthermore, when a hydrous gel having a low polymerization ratio is dried, a phenomenon that the hydrous gels adhere to each other to be integrated with each other arises during drying.

From the viewpoint of polymerization efficiency, the polymerization temperature Td is preferably equal to or higher than the 10-hour half-life temperature T10 of the used pyrolytic polymerization initiator. In the case where a plurality of polymerization initiators are used in combination, at least one of the polymerization initiators preferably satisfies the above range. Specifically, the difference $\Delta T2$ ($=Td-T10$) between the temperature Td and the temperature T10 is preferably not lower than 0° C., more preferably not lower than 5° C., further preferably not lower than 7° C., and particularly preferably not lower than 10° C. The upper limit of the difference $\Delta T2$ is preferably 20° C. from the viewpoint of energy efficiency.

By setting the above $\Delta T2$ within the above range, even when the monomer composition kept at a temperature lower than the temperature T10 is put into the organic solvent, a polymerization reaction is immediately initiated, and a high polymerization speed is achieved.

The temperature of the organic solvent in the reactor changes when the monomer composition is put into the reactor. In particular, temperature change is great in an area into which the monomer composition is put. Thus, preferably, the organic solvent heated by a heat exchanger is resupplied to this area, or the organic solvent in the reactor is heated by a temperature adjustment means such as a jacket provided on the reactor, such that a desired polymerization temperature Td is achieved in this area. Accordingly, temperature change of the organic solvent in the reactor that contributes to initiation or progress of the polymerization reaction is inhibited, and the polymerization temperature Td can be more accurately controlled.

(Polymerization Ratio)

In the method according to the present invention, from the viewpoint of inhibiting aggregation of the obtained hydrous gel during drying or reducing a residual monomer in the obtained water-absorbent resin, the polymerization ratio is preferably not less than 70% by mass, more preferably not less than 80% by mass, further preferably not less than 90% by mass, and particularly preferably not less than 95% by mass. The upper limit of the polymerization ratio is ideally 100% by mass. The polymerization ratio less than 70% by mass brings that the hydrous gels may strongly aggregate into a lump shape during drying, therefore that is not preferable.

(Reactor)

Figure 2:
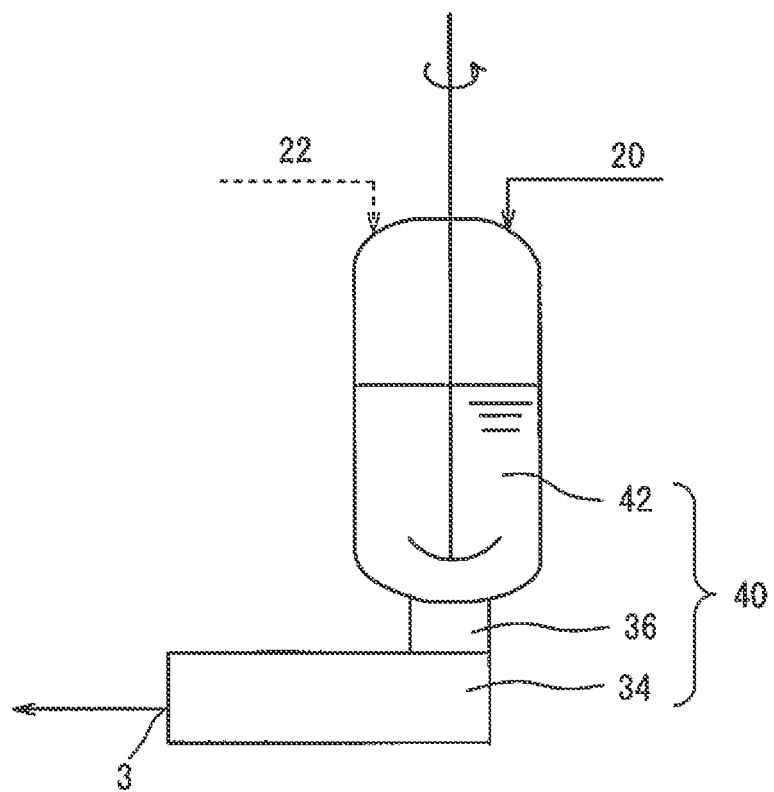
FIG. 2 is a schematic diagram showing a part of a process for producing a water-absorbent resin according to another embodiment of the present invention.

In the method for producing the water-absorbent resin according to the present invention, regarding the shape of the reactor in which the polymerization reaction is carried out, a conventionally known reactor shown in FIG. 2 can be used in the case where the polymerization step is batchwise. Meanwhile, a reactor shown in FIG. 1 is preferably used in the case where the polymerization step is continuous. Specifically, the shape of the reactor is a shape that allows the polymerization reaction to be carried out while the monomer composition is moving in the form of droplets in the organic solvent filling the reactor. An example of such a reactor is a reactor in which a tubular reaction tube is disposed vertically, horizontally, or helically. In this case, the ratio (L/D) of the inner diameter D (mm) to the length L (mm) of the reaction tube is preferably 2 to 100,000, more preferably 3 to 50,000, and further preferably 4 to 20,000.

By setting the ratio (L/D) within the above range, the droplets of the monomer composition favorably move within the reactor, and thus variations in the retention time of the droplets decrease. In addition, the particle diameter of the hydrous gel obtained finally has less variation, and thus the performance of the obtained water-absorbent resin also improves.

The reactor may be provided with a temperature adjustment means as necessary such that the organic solvent in the reactor can be heated or cooled from the outside. The organic solvent in the reactor is kept within a predetermined temperature range by the temperature adjustment means. Example of the temperature adjustment means include installation of a jacket, installation of a heater, installation of a temperature-maintaining material or a heat-insulating material, supply of hot air or cold air, to the reactor, and the like. The organic solvent to be resupplied to the reactor is heated by a heat exchanger.

As the material of the reactor, copper, a titanium alloy, stainless steel such as SUS304, SUS316, and SUS316L, fluororesins such as PTEE, PFA, and FEP, and the like can be used. Among them, from the viewpoint of adhesiveness of the obtained hydrous gel, fluororesins are preferable, and an inner wall surface of the reactor is more preferably subjected to surface treatment such as treatment with a fluororesin.

The hydrous gel produced in the polymerization step of the present invention may be separated from the organic solvent in the separation step after being partially dried in the organic solvent, or may be separated from the organic solvent in the separation step, not through the partial drying, after the polymerization. Preferably, a mode in which a shift is made from the polymerization step directly to the separation step, not through the partial drying, is preferable.

(Joint)

In the present invention, the reactor is connected to a later-described discharge device, for example, via a joint. The provision of the joint facilitates mounting the reactor to the discharge device and increases the flexibility in arrangement of the discharge device. For example, the discharge device can be disposed at a position other than the position directly below the reactor. For example, in the case where the flow direction of the hydrous gel is from the lower side to the upper side, the discharge device can be disposed above the reactor. In addition, by adjusting the length of the joint, the discharge device and the reactor can be installed so as to be away from each other. Moreover, for example, an upstream end portion of the joint may be formed in a shape corresponding to a lower end portion of the reactor, and a downstream end portion of the joint may be formed in a shape corresponding to an input port of the discharge device. As described above, the joint can increase the flexibility in arrangement between the reactor and the discharge device while maintaining a state where the reactor and the discharge device are directly connected. In the present specification, the "state where the reactor and the discharge device are directly connected" refers to a mode in which the organic solvent discharged from the reactor and containing at least the hydrous gel is supplied to the discharge device only via the joint. In addition, from the viewpoint of productivity, the joint is preferably configured such that the hydrous gel obtained in the reactor reaches the discharge device, disposed below or above the reactor, depending on balance between gravity and buoyancy, and more preferably configured such that the hydrous gel reaches the discharge device disposed below the reactor. Specifically, in a reaction device that includes the reactor, the joint, and the discharge device, the reactor, the joint, and the discharge device are preferably disposed such that the hydrous gel moves from the reactor through the joint to the discharge device due to gravity.

[2-4] Separation Step

This step is a step of extracting the hydrous gel produced in the polymerization step from the organic solvent. Preferably, in this step, the hydrous gel is separated from the organic solvent by extruding a slurry mixture (slurry liquid) containing the hydrous gel and the organic solvent while compressing the slurry mixture. This separation step includes transfer, compression, and discharge of the hydrous gel. The hydrous gel may be compressed while being transferred. That is, transfer and compression may simultaneously progress. Transfer and compression may be individually performed, and, for example, the hydrous gel may be compressed after being transferred, or may be transferred after being compressed. As one mode in the case where the hydrous gel is compressed after being transferred, a mode can be adopted in which the hydrous gel is transferred to the discharge port without being compressed, and is compressed when being discharged. Preferably, the hydrous gel is compressed while being transferred. Due to this compression, the hydrous gel and the organic solvent are separated from each other.

Preferably, in the separation step, the organic solvent is transferred in a direction opposite to the direction in which the hydrous gel is transferred. This point will be described in detail later.

(Transfer-Discharge Device (Discharge Device))

A transfer-discharge device (referred to as "discharge device" in the present specification) used in this step has a gel transfer mechanism that moves the hydrous gel from the input port of the discharge device toward the discharge port of the discharge device. In addition, the discharge device preferably has a gel compression mechanism that compresses the hydrous gel, and/or a pressure adjustment mechanism that adjusts pressure applied to the hydrous gel that is present at the discharge port. From the viewpoint of a decrease in residual liquid ratio and an improvement of liquid surface maintainability, a discharge device having a gel compression mechanism or a pressure adjustment mechanism is preferable, and a discharge device having a gel compression mechanism and a pressure adjustment mechanism is more preferable. In the discharge device, any one of the above mechanisms may serve as another mechanism, or the discharge device may have mechanisms that are independent from each other, as the above mechanisms.

The input port of the discharge device is also referred to as slurry liquid supply port. The discharge port of the discharge device is also referred to as hydrous gel discharge port. The discharge device has at least the one input port (slurry liquid supply port) and at least the one discharge port (hydrous gel discharge port).

(Gel Transfer Mechanism)

The gel transfer mechanism only needs to have a structure that can move the hydrous gel in a desired direction, for example, from the input port of the discharge device toward the discharge port of the discharge device. Specific examples of the gel transfer mechanism include a screw, a belt, a piston, a plunger, and the like. Among them, a screw that has continuous quantitative properties and that can provide a gel compression mechanism is preferable. In addition, a device using the screw is referred to as "screw extruder". The screw extruder includes, as main components, a shaft (hereinafter, referred to as "shaft portion") forming the screw, a helical blade (hereinafter, referred to as "flight portion") provided on an outer circumferential portion of the shaft, and a casing covering the shaft and the blade. A helical groove is formed on the shaft portion by the flight portion. The width of the groove is referred to as "pitch". The gap between the flight portion and the casing is referred to as "clearance". In addition, in the case where the screw extruder is used as the discharge device, the contents (slurry mixture) are pressed along the screw. Furthermore, a state where the contents are pressurized by the gel compression mechanism is sometimes referred to as "squeezed".

(Gel Compression Mechanism)

The gel compression mechanism only needs to have a structure that can compress the hydrous gel. Particularly, the gel compression mechanism preferably has a structure that can increase pressure applied to the hydrous gel while the hydrous gel is being moved by the gel transfer mechanism. The gel compression mechanism only needs to make a compression ratio greater than 1.

The term "compression ratio" refers to a value obtained by dividing the volume of the slurry, which is sucked by the discharge device per unit time, by the volume of the hydrous gel, containing the solvent, which can be discharged from the discharge device per unit time. In other words, in the case where the screw extruder is used as the discharge device, the term "compression ratio" refers to the ratio (V1/V2) of a volume (V1) per pitch at a supply portion of the screw relative to a volume (V2) per pitch at a discharge portion of the screw. The "supply portion of the screw" means a portion at the most upstream side (input port side) of the screw, and the "discharge portion of the screw" means a portion at the most downstream side (discharge port side) of the screw.

From the viewpoint of: promoting pressing out the organic solvent present between the gel particles; and decreasing the residual liquid ratio in the obtained water-absorbent resin, the compression ratio is preferably not less than 1.5, more preferably not less than 2, and further preferably not less than 5. In addition, in consideration of damage of the hydrous gel, the compression ratio is preferably not greater than 100, more preferably not greater than 70, and further preferably not greater than 50.

The gel compression mechanism in the present invention may be any mechanism that can achieve the above compression ratio. Specifically, a screw is preferable. In the case where the screw is used as the discharge device of the present invention, the screw serves as the above gel transfer mechanism and the above gel compression mechanism. In the screw, the compression ratio can be adjusted by changing individually the diameter of the above-described shaft portion, the height of the flight, the pitch, and the interval between the shaft portion and the casing as appropriate according to an advance direction of the hydrous gel. Examples of the gel compression mechanism include the following screw types.

(Type 1): a screw in which the pitch decreases with advancing toward the downstream side.

(Type 2): a (reverse taper type) screw in which the diameter of a shaft portion increases with advancing toward the downstream side.

(Type 3): a screw in which the height of a flight portion and/or the diameter of a shaft portion decreases with advancing toward the downstream side and the interval between the shaft portion and a casing decreases with advancing toward the downstream side.

(Type 4): a screw in which the number of shaft portions changes within the discharge device and the number of shaft portions at the upstream side is larger.

(Type 5): a combination of two or more types selected from the above (Type 1) to (Type 4).

Figure 3:
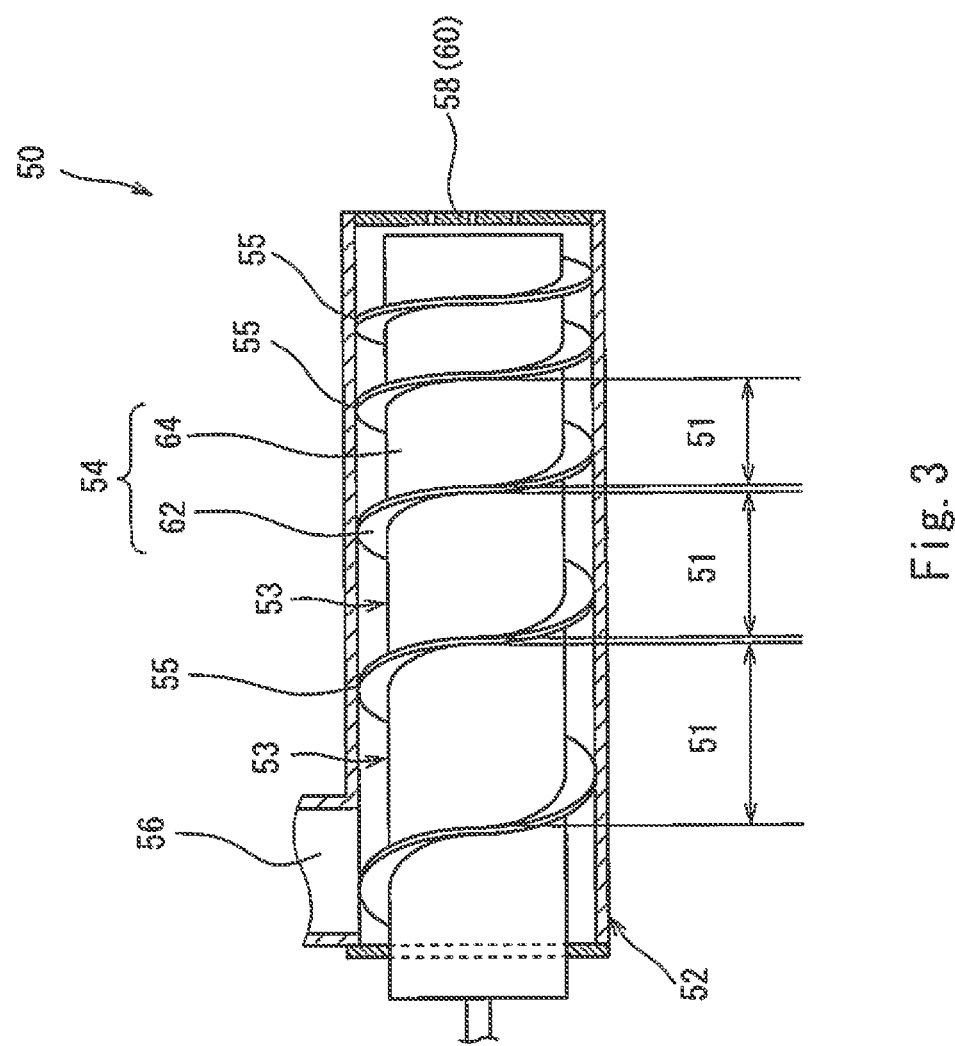
FIG. 3 is a schematic diagram showing a discharge device in which a pitch decreases with advancing in an advance direction and which has a multi-hole plate.
Figure 4:
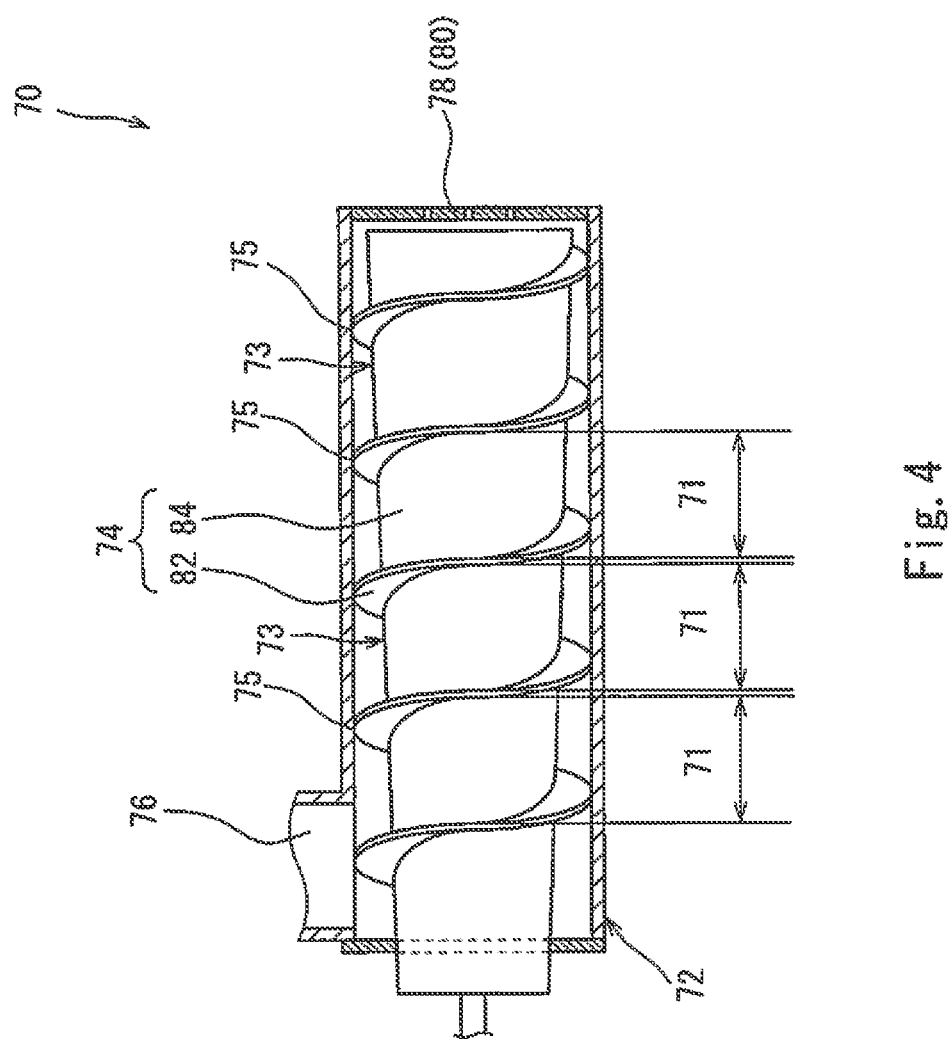
FIG. 4 is a schematic diagram showing a discharge device in which the diameter of a shaft portion of a screw increases with advancing in an advance direction and which has a multi-hole plate.
Figure 5:
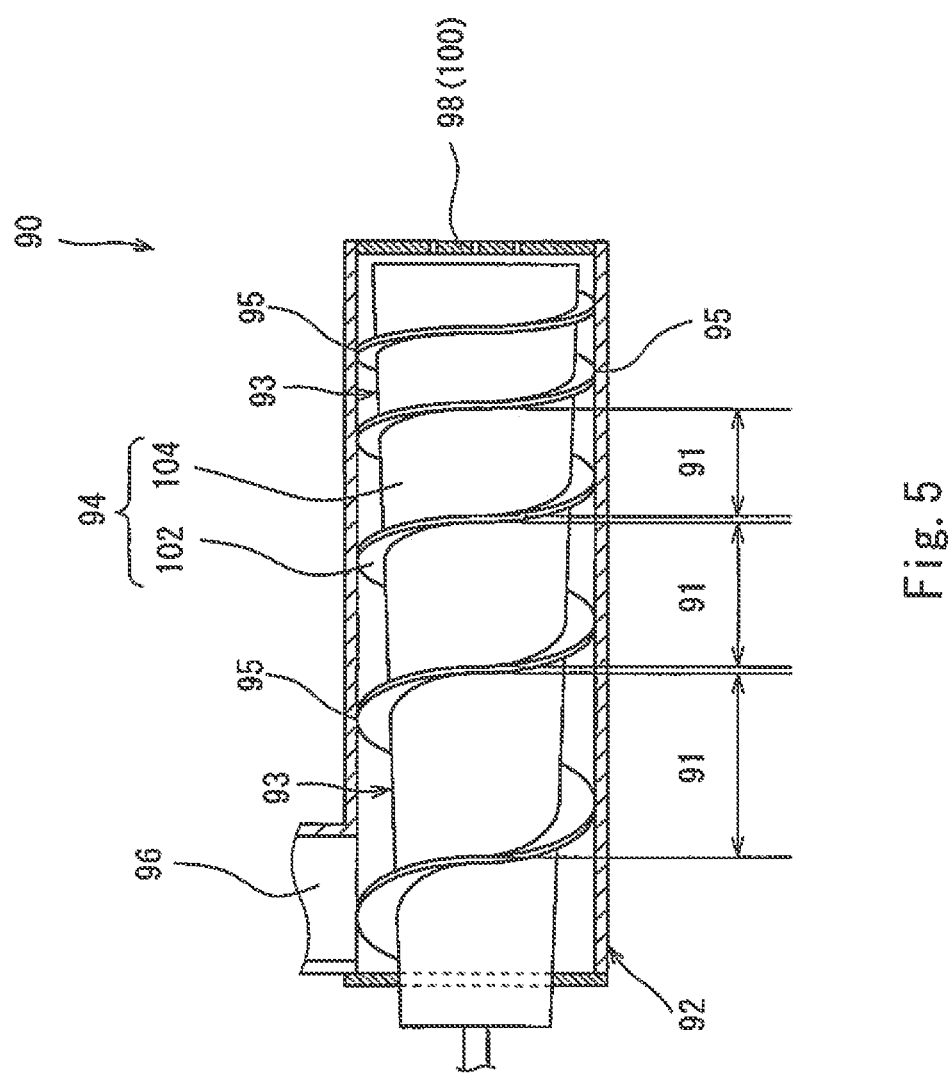
FIG. 5 is a schematic diagram showing a discharge device in which the diameter of a shaft portion of a screw increases and a pitch decreases with advancing in an advance direction and which has a multi-hole plate.
Figure 9:
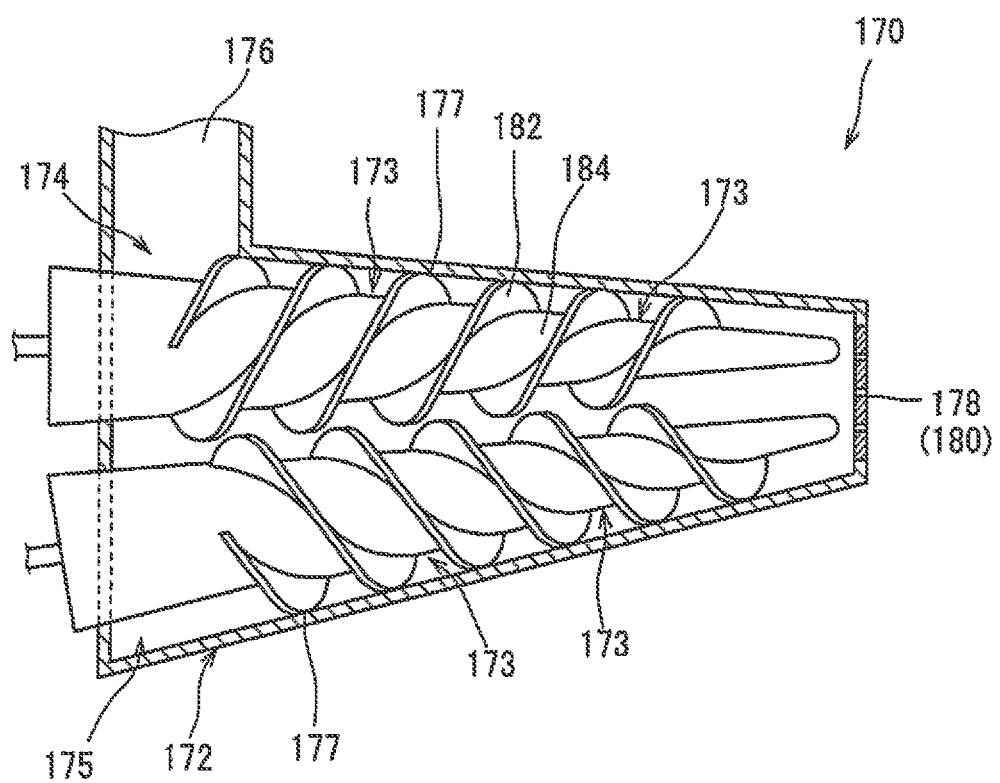
FIG. 9 is a schematic diagram showing a discharge device which has twin screws and a multi-hole plate and in which the inner diameter of a casing and the diameters of shaft portions decrease with advancing in an advance direction.
Figure 10:
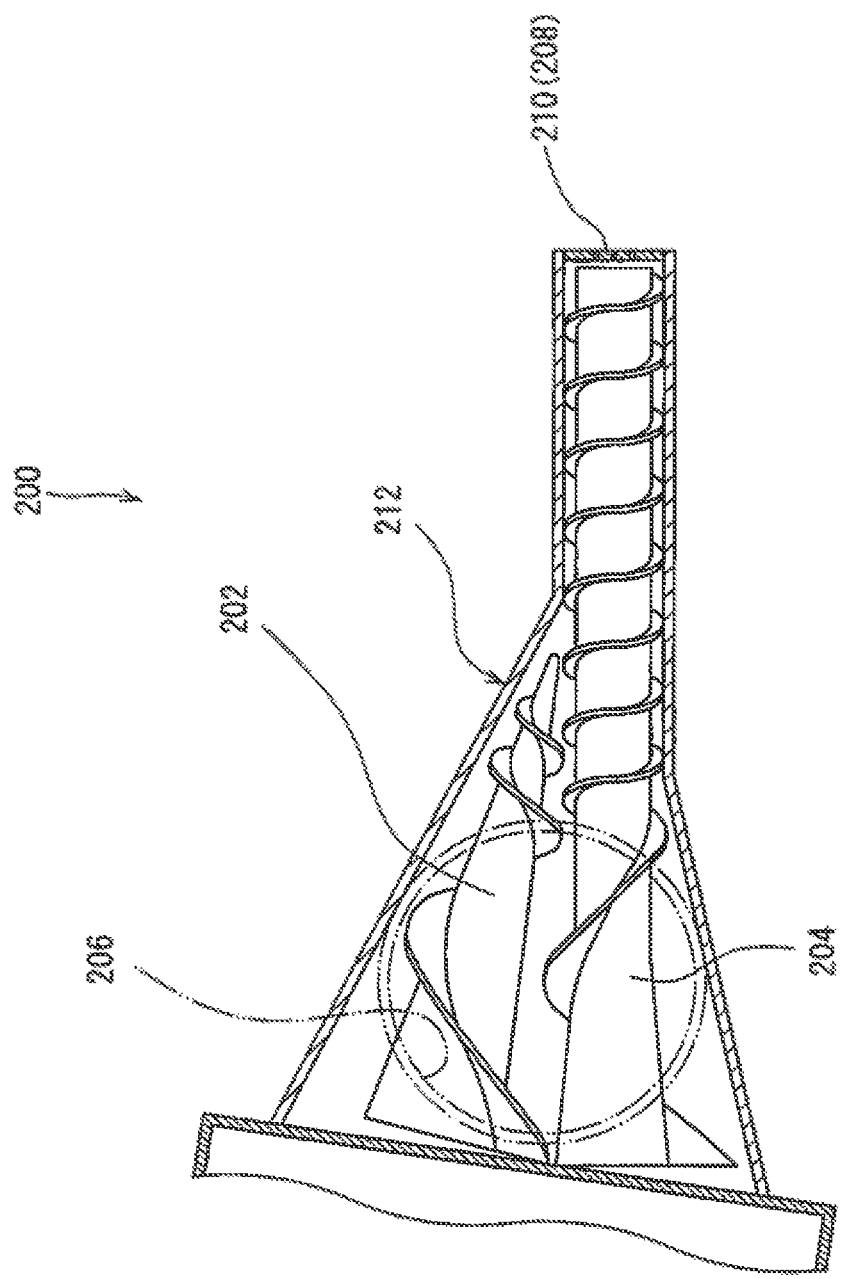
FIG. 10 is a schematic diagram showing a discharge device having a twin-single screw structure.

A specific example of the above Type 1 is a screw in which the diameters of the shaft portion and the casing are uniform but the pitch decreases with advancing toward the downstream side (FIG. 3). A specific example of the above Type 2 is a reverse taper type screw in which the inner diameter of the casing and the pitch are uniform but the diameter of the shaft portion increases with advancing toward the downstream side (FIG. 4). Specific examples of the above Type 3 include a single screw in which the height of the flight portion (the inner diameter of the casing) decreases with advancing toward the downstream side (FIG. 7), a single screw in which the diameter of the shaft portion and the inner diameter of the casing decrease with advancing toward the downstream side (FIG. 8), and a twin screw in which the diameters of each shaft portion and the inner diameter of the casing decrease with advancing toward the downstream side (FIG. 9). A specific example of the above Type 4 is a twin-single taper screw (FIG. 10). A specific example of the above Type 5 is a screw in which the shaft portion is reversely tapered and the pitch decreases with advancing toward the downstream side (FIG. 5).

The gel compression mechanism may be configured in a form other than the above screw. Examples of the gel compression mechanism include a plunger that pushes out the hydrous gel from the input port toward the discharge port at regular intervals, a belt having a gradually decreasing interval from the casing, and the like.

(Pressure Adjustment Mechanism)

The pressure adjustment mechanism only needs to have a structure that can adjust pressure applied to the hydrous gel at the discharge port of the discharge device.

An example of the pressure adjustment mechanism is a back pressure plate. The back pressure plate adjusts pressure applied to the hydrous gel, while limiting the opening area of the discharge port, by being pressed against the discharge port at predetermined pressure. Certain pressure is preferably applied to the back pressure plate by a pressure application device such as an air cylinder and a hydraulic cylinder. As the back pressure plate, known one is used.

Other examples of the pressure adjustment mechanism include a single-hole plate or a multi-hole plate having pressure adjustment hole(s). Another example of the pressure adjustment mechanism is a die. The number of pressure adjustment holes is not limited, and at least one pressure adjustment hole only needs to be provided. By using, as the discharge port, the single-hole plate or the multi-hole plate having pressure adjustment hole(s), and changing the diameters, the number, and the hole area ratio of pressure adjustment holes, and the like, the pressure applied to the hydrous gel is adjusted. Among the drawings of the present application, the back pressure plate is installed only in FIG. 6, but in the other embodiments (FIGS. 4, 5, and 7 to 10), the multi-hole plate can be replaced with the back pressure plate. In the case where the single-hole plate or the multi-hole plate having pressure adjustment hole(s) is used, the hole area ratio thereof (sum of hole areas/entire cross-sectional area of discharge port)×100) is preferably 10% to 80%. The hole diameters are preferably 1 mm to 20 mm. When the hole area ratio and the hole diameters of the pressure adjustment holes fall within the above ranges, the hydrous gel and the organic solvent can be efficiently separated from each other. Thus, the above ranges are preferable.

From the viewpoint of: promoting pressing out the organic solvent present between the gel particles; and decreasing the residual liquid ratio in the obtained water-absorbent resin, the pressure applied to the hydrous gel is preferably not less than 0.1 MPa, more preferably not less than 0.2 MPa, and further preferably not less than 0.3 MPa. In addition, in consideration of damage of the hydrous gel, the pressure applied to the hydrous gel is preferably not greater than 2 MPa, more preferably not greater than 1.5 MPa, and further preferably not greater than 1 MPa. Preferably, the pressure is the pressure at the discharge port. In the case where the gel compression mechanism and the pressure adjustment mechanism are provided, the pressure is preferably measured in the hydrous gel present between the pressure adjustment mechanism and an end portion at the most downstream side of the gel compression mechanism. In addition, the pressure applied to the hydrous gel can also be adjusted on the basis of the amount of the hydrous gel supplied to the discharge device per unit time, the operating conditions of the gel transfer mechanism (for example, the rotation speed of the screw), and the like.

(Other Structures and Mechanisms)

The above Types 1 to 5 have been described as examples of the case where the screw extruder is used as the discharge device of the present invention. With any of these Types, the gap (clearance) between the flight portion and the casing is preferably uniform. The clearance is preferably 0.1 mm to 3 mm, more preferably 0.2 mm to 2 mm, and further preferably 0.5 mm to 1.5 mm. When the clearance is greater than 3 mm, the hydrous gel may flow back, so that the performance of separation from the organic solvent may decrease. On the other hand, when the clearance is less than 0.1 mm, the flight portion and the casing may come into contact with each other due to vibration of the shaft portion caused by rotation of the screw, so that trouble such as breakdown of the device may occur.

The material of the casing may be metal or may be resin. Furthermore, although not shown, the casing may be a cylindrical member having multiple filtration holes (hereinafter, sometimes referred to as "filtration cylinder"). An example of the filtration cylinder is a member obtained by forming a punched plate in a cylindrical shape. In addition, a member having the same effect as the filtration holes, or a member that has mechanical strength enough to withstand the above pressure and that has a function to prevent the hydrous gel from passing therethrough and allow only the organic solvent to pass therethrough, can be used as the casing. For example, the casing may be formed as a screen-like cylinder using a wedge wire (a wire having a wedge-shaped cross-section), a screen, a mesh, a filter, or the like. As described above, a known screw press may be used as the transfer-discharge device of the present invention.

(Transfer/Discharge Method)

In the case where the screw extruder is used as the discharge device in the separation step of the present invention, the hydrous gel and the organic solvent are continuously taken into the screw extruder. By rotation of the screw, the hydrous gel is continuously transferred from the input port of the screw extruder to the discharge portion of the screw extruder. The sequentially transferred hydrous gel is finally discharged through the discharge port.

The separation step includes transfer, compression, and discharge of the hydrous gel. With the transfer, the hydrous gel is preferably compressed. With the compression of the hydrous gel, the organic solvent is pressed out from the hydrous gel. That is, the hydrous gel is squeezed. The pressed-out organic solvent flows to the low pressure side, that is, the input port side, without being restrained by the screw. On the other hand, the hydrous gel restrained by the screw is transferred to the discharge port side by rotation of the screw. As described above, within the discharge device, the organic solvent flows in the direction opposite to the direction in which the hydrous gel is transferred. In other words, the organic solvent flows backward within the discharge device. The transferred hydrous gel is discharged through the discharge port. The compressed hydrous gel is continuously discharged through the discharge port. Since the organic solvent is pressed out by the compression, the residual liquid ratio of the discharged hydrous gel is low. The discharged hydrous gel is supplied to the next step (for example, a drying step). This supply is continuous. The organic solvent pressed out from the hydrous gel flows backward, is discharged through the input port, and reused.

Specifically, when the slurry liquid containing the hydrous gel moves from the slurry liquid supply port (input port) to the hydrous gel discharge port (discharge port), the pressure applied to the slurry liquid rises, and also separation between the hydrous gel and the dispersion medium (organic solvent) progresses. The separated dispersion medium moves in the direction toward the slurry liquid supply port, and the hydrous gel is discharged through the hydrous gel discharge port.

Due to the above compression, back pressure is applied to the hydrous gel at the discharge port side of the discharge device. On the other hand, liquid pressure is applied at the input port of the discharge device due to the mass of the liquid in the reactor (and the joint). For example, in the case where the reactor is a vertical type reaction tower and the discharge device is located below the reactor, the liquid pressure is high since the position of the liquid surface within the reactor is high. In the case where the discharge device is directly connected to the reactor, the organic solvent may flow out from the discharge port of the discharge device due to the liquid pressure. However, since the back pressure is higher than the liquid pressure, flow of the solvent to the discharge port is prevented. In addition, since the hydrous gel is discharged through the discharge port, the compressed hydrous gel forms a layer in the vicinity of the discharge port. Thus, the solvent does not substantially flow out from the discharge port. Therefore, even when the discharge device is directly connected to the reactor, it is easy to maintain the liquid surface in the reactor.

The hydrous gel is continuously transferred toward the discharge port by the screw. As a result, the hydrous gel forms a layer while being compressed toward the discharge port, and is discharged through the discharge port. By the layer of the compressed hydrous gel, the back pressure at the discharge port is maintained. In particular, in the case of a continuous polymerization step, maintenance of the back pressure at the discharge port contributes to inhibition of fluctuations of the liquid surface height in the reactor.

As described above, in the discharge device in which the hydrous gel is compressed by the screw, the device related to the separation step (the discharge device) can be connected to the reactor and can further be directly connected thereto. As described above, this connection facilitates supply of the hydrous gel to the separation step and contributes to improvement of productivity.

In a preferable discharge device, openings are only an input port and a discharge port. In this case, since the layer of the hydrous gel compressed toward the discharge port is formed, outflow of the organic solvent through the discharge port is minimized. That is, the reaction device including the preferable discharge device has less loss of the organic solvent since the organic solvent is unlikely to flow out of the reaction device in separation between the organic solvent and the hydrous gel. In other words, in the embodiment of the present invention, the reactor, the joint, and the discharge device are connected in this order, and a structure is preferably provided in which the contents cannot flow out to or flow in from the outside unless pipes or the like are provided between these devices.

The discharge device having the screw is used for a batchwise production method and also used for a continuous production method. In particular, the discharge device having the screw is preferably used for a continuous production method. The hydrous gel can be continuously taken in and continuously discharged by the screw, and thus the hydrous gel can be continuously separated. In addition, due to the direct connection, the hydrous gel produced in the reactor can continuously reach the discharge device. In the case where the reaction step is continuous, the synergetic effect with continuity of the separation step is exerted, so that the production efficiency of the reaction device improves.

A known screw extruder can be used as the discharge device. The screw extruder is used for the purpose of molding or kneading resin. The present inventors have found that the extruder can be used for a totally different purpose, that is, in a separation step of separating a hydrous gel and a solvent from each other in production of a water-absorbent resin. The present inventors have found that the use of the screw extruder provides advantages such as a decrease in residual liquid ratio due to compression, less loss of an organic solvent, and continuity of separation.

The pressure and shear stress applied by the extruder (discharge device) may damage the hydrous gel. However, it is found that in actuality, the water absorption performance and physical properties of the water-absorbent resin obtained finally can be adjusted as appropriate on the basis of not only the operating conditions such as polymerization conditions but also conditions for the separation method of the present invention.

(Specific Embodiments of Discharge Device)

A discharge device used in Example 1 described below will be described with reference to FIG. 3. FIG. 3 is a schematic diagram of the interior of a screw extruder 50 used in Example 1 as seen from the lateral side. The screw extruder 50 includes a casing 52, a screw 54, an input port 56, and a discharge port 58. A multi-hole plate 60 is provided at the discharge port 58. The multi-hole plate 60 is provided with a plurality of through holes (pressure adjustment holes). The discharge port 58 is closed by the multi-hole plate 60. The screw 54 has a flight portion 62 and a shaft portion 64. The shaft portion 64 has a uniform (straight) outer diameter. The flight portion 62 is provided on the outer circumferential surface of the shaft portion 64 and helically extends. The flight portion 62 and the shaft portion 64 form a groove 53 having a side surface formed by the flight portion 62 and a bottom surface formed by the shaft portion 64. The flight portion 62 has a pitch 51 that decreases when approaching the discharge port 58. The pitch 51 is measured along an axial direction. The axial direction is the direction of the center line of the shaft portion 64. A clearance (gap) 55 is provided between the casing 52 and the flight portion 62. The clearance 55 is uniform. The casing 52 does not allow the organic solvent to pass therethrough.

A discharge device used in Example 2 described below will be described with reference to FIG. 4. FIG. 4 is a schematic diagram of the interior of a screw extruder 70 used in Example 2 as seen from the lateral side. The screw extruder 70 includes a casing 72, a screw 74, an input port 76, and a discharge port 78. A multi-hole plate 80 is provided at the discharge port 78. The multi-hole plate 80 is provided with a plurality of through holes (pressure adjustment holes). The discharge port 78 is closed by the multi-hole plate 80. The screw 74 has a flight portion 82 and a shaft portion 84. The shaft portion 84 is reversely tapered. That is, the shaft portion 84 has an outer diameter that increases when approaching the discharge port 78. The flight portion 82 is provided on the outer circumferential surface of the shaft portion 84 and helically extends. The flight portion 82 and the shaft portion 84 form a groove 73 having a side surface formed by the flight portion 82 and a bottom surface formed by the shaft portion 84. The flight portion 82 has a uniform pitch 71. A clearance (gap) 75 is provided between the casing 72 and the flight portion 82. The clearance 75 is uniform. The casing 72 does not allow the organic solvent to pass therethrough.

A discharge device used in Example 3 described below will be described with reference to FIG. 5. FIG. 5 is a schematic diagram of the interior of a screw extruder 90 used in Example 3 as seen from the lateral side. The screw extruder 90 includes a casing 92, a screw 94, an input port 96, and a discharge port 98. A multi-hole plate 100 is provided at the discharge port 98. The multi-hole plate 100 is provided with a plurality of through holes (pressure adjustment holes). The discharge port 98 is closed by the multi-hole plate 100. The screw 94 has a flight portion 102 and a shaft portion 104. The shaft portion 104 is reversely tapered. That is, the shaft portion 104 has an outer diameter that increases when approaching the discharge port 98. The flight portion 102 is provided on the outer circumferential surface of the shaft portion 104 and helically extends. The flight portion 102 and the shaft portion 104 form a groove 93 having a side surface formed by the flight portion 102 and a bottom surface formed by the shaft portion 104. The flight portion 102 has a pitch 91 that decreases when approaching the discharge port 98. A clearance (gap) 95 is provided between the casing 92 and the flight portion 102. The clearance 95 is uniform. The casing 92 does not allow the organic solvent to pass therethrough.

A discharge device used in Example 4 described below will be described with reference to FIG. 10. FIG. 10 is a schematic diagram of the interior of a screw extruder 200 used in Example 4 as seen from above. The screw extruder 200 includes a first screw 202, a second screw 204, an input port 206, a discharge port 208, a multi-hole plate 210, and a casing 212. The first screw 202 extends from the input port 206 to the discharge port 208. The second screw 204 is located at the input port 206 and terminates without reaching the discharge port 208. The second screw 204 has a shaft portion with a tapered shape. The second screw 204 is disposed along the first screw 202. The casing 212 does not allow the organic solvent to pass therethrough.

The following will describe discharge devices that can be used in Examples, as modifications, with reference to FIGS. 6 to 9.

Figure 6:
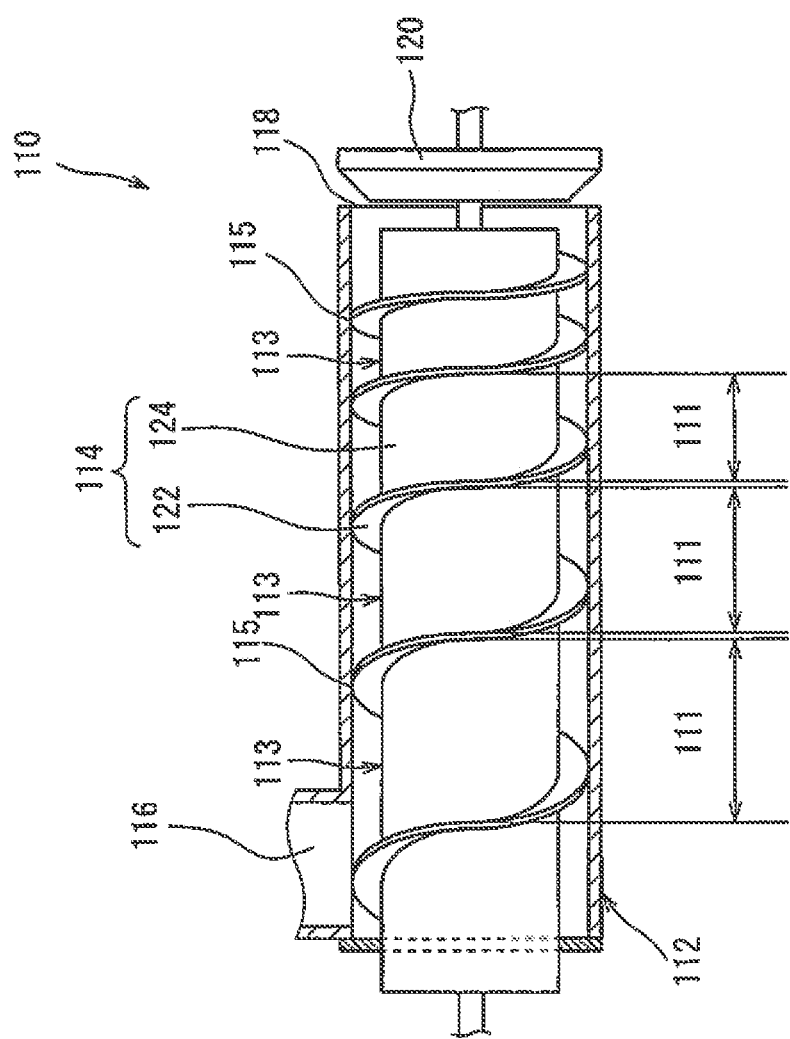
FIG. 6 is a schematic diagram showing a discharge device in which a pitch decreases with advancing in an advance direction and which has a back pressure plate.

FIG. 6 is a schematic diagram of the interior of a screw extruder 110 according to a modification as seen from the lateral side. The screw extruder 110 includes a casing 112, a screw 114, an input port 116, and a discharge port 118. A back pressure plate 120 is provided at the discharge port 118. Although not shown, the back pressure plate 120 includes a pressure application device (air cylinder). The back pressure plate 120 is also referred to as air cylinder type back pressure plate. By the back pressure plate 120 being pressed against the discharge port 118 by the pressure application device, pressure applied to a hydrous gel is adjusted while the opening area of the discharge port 118 is limited. The screw 114 has a flight portion 122 and a shaft portion 124. The shaft portion 124 has a uniform outer diameter. The flight portion 122 is provided on the outer circumferential surface of the shaft portion 124 and helically extends. The flight portion 122 and the shaft portion 124 form a groove 113 having a side surface formed by the flight portion 122 and a bottom surface formed by the shaft portion 124. The flight portion 122 has a pitch that decreases when approaching the discharge port 118. A clearance (gap) 115 is provided between the casing 112 and the flight portion 122. The clearance 115 is uniform. The casing 112 does not allow the organic solvent to pass therethrough.

Figure 7:
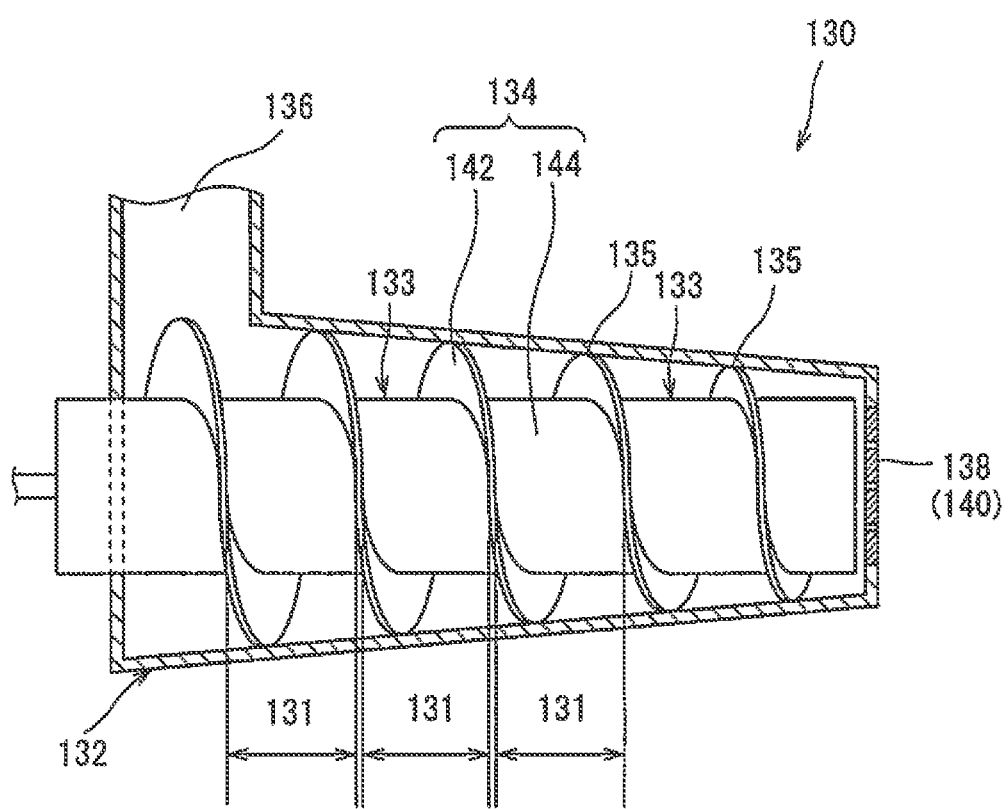
FIG. 7 is a schematic diagram showing a discharge device in which the inner diameter of a casing decreases with advancing in an advance direction and which has a multi-hole plate.

FIG. 7 is a schematic diagram of a screw extruder 130 according to another modification as seen from the lateral side. The screw extruder 130 includes a casing 132, a screw 134, an input port 136, and a discharge port 138. A multi-hole plate 140 is provided at the discharge port 138. The casing 132 has an inner diameter that decreases when approaching the discharge port 138. The multi-hole plate 140 is provided with a plurality of through holes (pressure adjustment holes). The discharge port 138 is closed by the multi-hole plate 140. The screw 134 has a flight portion 142 and a shaft portion 144. The shaft portion 144 has a uniform outer diameter. The flight portion 142 is provided on the outer circumferential surface of the shaft portion 144 and helically extends. The flight portion 142 has a height that decreases when approaching the discharge port 138. The flight portion 142 and the shaft portion 144 form a groove 133 having a side surface formed by the flight portion 142 and a bottom surface formed by the shaft portion 144. The flight portion 142 has a uniform pitch 131. A clearance (gap) 135 is provided between the casing 132 and the flight portion 142. The clearance 135 is uniform. The casing 132 does not allow the organic solvent to pass therethrough.

Figure 8:
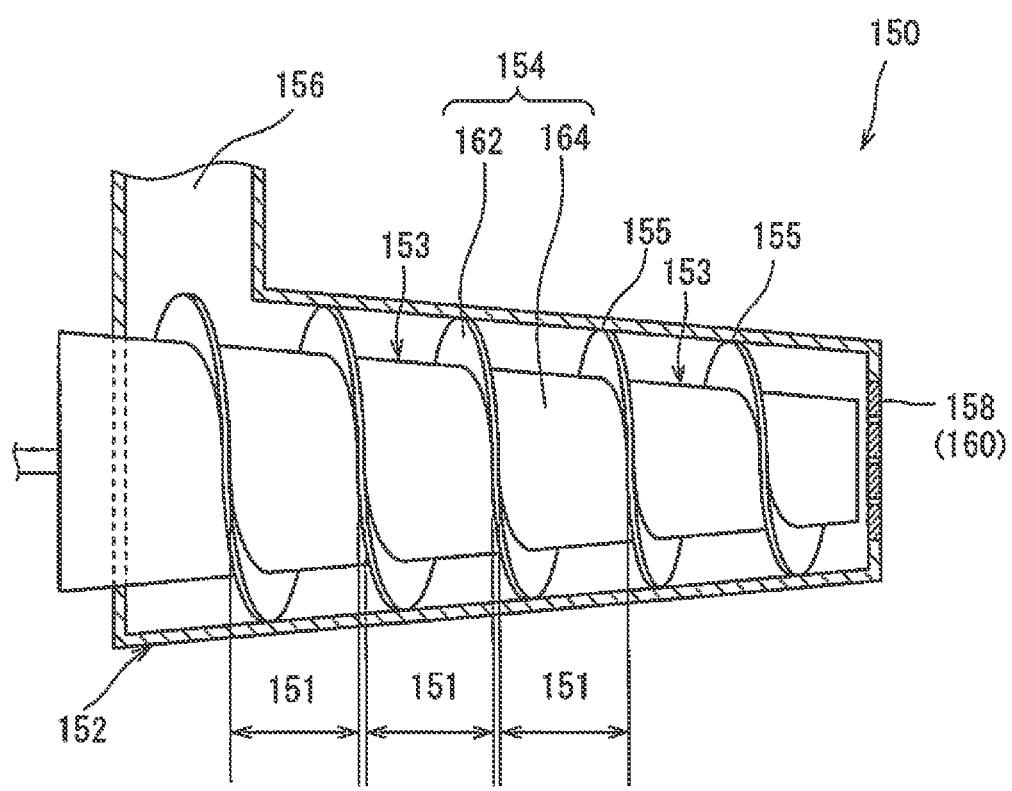
FIG. 8 is a schematic diagram showing a discharge device in which the inner diameter of a casing and the diameter of a shaft portion decrease with advancing in an advance direction and which has a multi-hole plate.

FIG. 8 is a schematic diagram of a screw extruder 150 according to still another modification as seen from the lateral side. The screw extruder 150 includes a casing 152, a screw 154, an input port 156, and a discharge port 158. A multi-hole plate 160 is provided at the discharge port 158. The casing 152 has an inner diameter that decreases when approaching the discharge port 158. The multi-hole plate 160 is provided with a plurality of through holes (pressure adjustment holes). The discharge port 158 is closed by the multi-hole plate 160. The screw 154 has a flight portion 162 and a shaft portion 164. The shaft portion 164 has an outer diameter that decreases when approaching the discharge port 158. The flight portion 162 is provided on the outer circumferential surface of the shaft portion 164 and helically extends. The flight portion 162 has a uniform height. The flight portion 162 and the shaft portion 164 form a groove 153 having a side surface formed by the flight portion 162 and a bottom surface formed by the shaft portion 164. The flight portion 162 has a uniform pitch 151. A clearance (gap) 155 is provided between the casing 152 and the flight portion 162. The clearance 155 is uniform. The casing 152 does not allow the organic solvent to pass therethrough.

FIG. 9 is a schematic diagram of a screw extruder 170 according to still another modification as seen from the lateral side. The screw extruder 170 includes twin screws. The screw extruder 170 includes a casing 172, a first screw 174, a second screw 175, an input port 176, and a discharge port 178. A multi-hole plate 180 is provided at the discharge port 178. The casing 172 has an inner diameter that decreases when approaching the discharge port 178. The casing 172 does not allow the organic solvent to pass therethrough. The multi-hole plate 180 is provided with a plurality of through holes (pressure adjustment holes). The discharge port 178 is closed by the multi-hole plate 180. The first screw 174 has a flight portion 182 and a shaft portion 184. The shaft portion 184 has an outer diameter that decreases when approaching the discharge port 178. The flight portion 182 is provided on the outer circumferential surface of the shaft portion 184 and helically extends. The flight portion 182 has a uniform height. The flight portion 182 and the shaft portion 184 form a groove 173 having a side surface formed by the flight portion 182 and a bottom surface formed by the shaft portion 184. The flight portion 182 has a uniform pitch. A clearance (gap) 177 is provided between the casing 172 and the flight portion 182. The clearance 177 is uniform. The configuration of the second screw 175 is the same as that of the first screw 174 except the direction of the helix of the flight portion is opposite to that of the first screw 174. The interval between the central axis of the first screw 174 and the central axis of the second screw 175 decreases when approaching the discharge port 178.

(Transfer-Separation Device of Comparative Example)

FIG. 11 is a schematic diagram of the interior of a screw feeder 220 used in Comparative Example 1 as seen from the lateral side. The screw feeder 220 includes a casing 222, a screw 224, an input port 226, and a discharge port 228. The entirety of the discharge port 228 is opened. The casing 222 has a uniform inner diameter. The screw 224 has a flight portion 232 and a shaft portion 234. The shaft portion 234 has a uniform outer diameter. The flight portion 232 is provided on the outer circumferential surface of the shaft portion 234 and helically extends. The flight portion 232 has a uniform height. The flight portion 232 and the shaft portion 234 form a groove 223 having a side surface formed by the flight portion 232 and a bottom surface formed by the shaft portion 234. The flight portion 232 has a uniform pitch 221. The screw feeder shown in FIG. 11 is a device that transfers contents, does not have a compression mechanism, and is different in this point from the screw extruder used in the present invention.

Specific Embodiments

FIG. 1 shows a part (a mixing step to a separation step) of a process for producing a water-absorbent resin according to an embodiment of the present invention. As shown, in this production process, a mixing device 10, a supply device 12, a reaction device 14, a heat exchanger 16, a liquid-feeding pump 18, and a pipe 20 and pipes 30 that connect between these devices are included. In addition, a monomer aqueous solution and a polymerization initiator are supplied to the mixing device 10 through pipes 1 and 2, respectively. The reaction device 14 includes a reactor 32, a discharge device 34, and a joint 36. The joint 36 connects the reactor 32 and the discharge device 34 to each other. The reactor 32, the joint 36, the heat exchanger 16, and the pipes 30 are filled with an organic solvent.

The reaction device 14 is a reaction device in which a polymerization reaction of the monomer composition is carried out, and includes the reactor 32, the joint 36, and the discharge device 34. That is, a polymerization step and the separation step are performed with the reaction device 14. A hydrous gel obtained in the polymerization step is discharged from the discharge device 34. That is, the present invention includes a method for producing a water-absorbent resin using the reaction device 14. The reaction device 14 is an example of a continuous reverse phase suspension polymerization reaction device.

The discharge device (transfer-discharge device) 34 is a separation device that separates the hydrous gel from the organic solvent.

The discharge device 34 is included in the reaction device 14. The discharge device 34 is connected to the reactor 32. Furthermore, the discharge device 34 is directly connected to the reactor 32. In this embodiment, the joint 36 is present. In such a case, in the present application, the reactor 32 and the discharge device 34 are interpreted to be directly connected to each other. This direct connection will be described in detail later.

An outline of the method for producing the water-absorbent resin of the present invention will be described with reference to FIG. 1.

First, in a state where the discharge port of the discharge device 34 is closed, the interiors of the reaction device 14, the heat exchanger 16, and the pipes 30 that connects these devices are filled with the organic solvent, and the liquid-feeding pump 18 is activated to circulate the organic solvent therethrough. The organic solvent in each device and each pipe is heated to a predetermined temperature by the heat exchanger 16. A part of the organic solvent heated by the heat exchanger 16 is also supplied to the supply device 12.

Next, the monomer aqueous solution and the pyrolytic polymerization initiator which are separately prepared are individually and continuously supplied to the mixing device 10 and mixed with each other to prepare a monomer composition. Thereafter, the monomer composition is continuously supplied to the supply device 12 through the pipe 20. The monomer composition is continuously put into the organic solvent in the reactor 32 in the form of droplets by the supply device 12, and a polymerization reaction is initiated in the reactor 32. In the reactor 32, because of the movement of the circulated organic solvent, the droplets formed with the monomer composition move. The droplets turn into a hydrous gel by the polymerization reaction while moving. The movement direction of the droplets and the hydrous gel is the same as the movement direction of the organic solvent (parallel flow). In the present application, a polymerization method in which a polymerization reaction is initiated to obtain a hydrous gel in a state where droplets containing the monomer are dispersed or suspended in a liquid phase composed of the organic solvent, is referred to as liquid phase droplet polymerization. The liquid phase droplet polymerization is an example of reverse phase suspension polymerization. In the case where the liquid phase droplet polymerization is continuously carried out as in the above embodiment, this polymerization method is referred to as liquid phase droplet continuous polymerization. The liquid phase droplet continuous polymerization is an example of continuous reverse phase suspension polymerization. The reverse phase suspension polymerization may be discontinuous. The liquid phase droplet polymerization may be discontinuous.

The hydrous gel produced by the above polymerization moves along the flow of the circulated organic solvent, and settles or floats depending on balance between gravity and buoyancy. When the hydrous gel settles, the hydrous gel is naturally (automatically) supplied from the reactor 32 through the joint 36 to the discharge device 34. The hydrous gel that has reached the input port of the discharge device 34 is continuously taken into the discharge device 34 together with the organic solvent.

The hydrous gel and the organic solvent taken into the discharge device 34 are transferred toward the discharge port by rotation of the screw in the discharge device. By using the screw, the hydrous gel is continuously transferred. The discharge device 34 has a gel compression mechanism that increases the degree of compression of the hydrous gel with progress of transfer. Thus, with the transfer, the hydrous gel is compressed. As the hydrous gel is transferred, the hydrous gel is compressed, and the pressure applied to the hydrous gel increases. The compressed hydrous gel is discharged through a discharge port 3. The continuously transferred hydrous gel is continuously discharged.

As described above, the discharge device 34 is connected to the reactor 32. That is, the slurry liquid supply port (input port) of the discharge device 34 and the product discharge port of the reactor in which continuous reverse phase suspension polymerization is carried out are connected to each other. The concept of this "connection" is a broad concept including "direct connection". Even in the case where a device that hinders movement of the hydrous gel is provided between the reactor 32 and the discharge device 34, when the reactor 32 and the discharge device 34 are coupled with each other, this state corresponds to the "connection". For example, a pump may be provided between the reactor 32 and the discharge device 34. This connection facilitates supply of the produced hydrous gel to the discharge device.

As described above, the discharge device 34 is directly connected to the reactor 32. This "direct connection" is defined as follows. A state where the hydrous gel produced in the reactor 32 can move in the organic solvent and reach the input port of the discharge device 34 is a state where "the discharge device 34 is directly connected to the reactor 32". Thus, for example, in the case where the joint 36 is a pipe, even when the pipe is tilted, this state can correspond to the "direct connection", and even when the pipe is bent, this state can correspond to the "direct connection". Even when the discharge device 34 is not located directly below the reactor 32 in the vertical direction, this state can correspond to the "direct connection". For example, even when the input port of the discharge device 34 is located above the product discharge port of the reactor 32 in the vertical direction, this state can correspond to the "direct connection". For example, when the internal pressure of the reactor 32 is high, the hydrous gel can naturally reach the discharge device 34 that is located above the reactor 32 in the vertical direction. Preferably, the hydrous gel produced in the reactor 32 can reach the input port of the discharge device 34 due to gravity sedimentation. The direct connection facilitates supply of the hydrous gel to the discharge device 34, and thus productivity improves. For example, the hydrous gel produced in the reactor 32 can be automatically supplied to the discharge device 34 due to gravity. Thus, work for supplying the hydrous gel to the separation step can be unnecessary. In addition, in the case of a continuous type, the separated organic solvent flows backward in the discharge device 34, is naturally discharged through the input port, returns to the circulation system, and is reused.

In another embodiment of the present invention, batchwise production in which the monomer composition is intermittently supplied into the organic solvent in the reaction device is also possible. In this case, a batchwise stirring type reaction device is used as the reaction device. For example, the discharge device 34 may be directly connected to a lower portion of a reaction tank in the batchwise stirring type reaction device. The above liquid phase droplet polymerization includes the above batchwise production.

FIG. 2 shows a part (a supplying step to a separation step) of a process for producing a water-absorbent resin according to another embodiment. In the embodiment in FIG. 2, a batchwise reaction device 40 is used. As shown, this process includes the reaction device 40 and a pipe 20. The reaction device 40 includes a reactor 42, a discharge device 34, and a joint 36. The joint 36 connects the reactor 32 and the discharge device 34 to each other. An organic solvent is stored in the reaction device 40. The joint 36 is filled with the organic solvent.

The pipe 20 is an example of the above-described supply device. A monomer composition is supplied to the reactor 42 through the pipe 20. A monomer aqueous solution and a polymerization initiator may be individually supplied to the reactor 42. For example, as shown in FIG. 2, the monomer aqueous solution may be supplied through the first pipe 20, and the polymerization initiator may be supplied through a second pipe 22 (shown by a broken line). Similar to the case of the above-described continuous type, the monomer composition may be supplied in the form of droplets. In addition, a mixed liquid obtained by mixing the monomer composition and the organic solvent in advance may be supplied.

The reaction device 40 is a reaction device in which a polymerization reaction of the monomer composition is carried out, and includes the discharge device 34. A polymerization step and the separation step are performed with the reaction device 40. As described above, the discharge device 34 is a separation device that separates a hydrous gel from the organic solvent. The discharge device 34 is included in the batchwise reaction device 40. The discharge device 34 is directly connected to the reactor 42.

Preferably, the reaction device 40 has a stirring mechanism that can stir the organic solvent within the reactor 42 (see FIG. 2). The monomer composition (or the monomer aqueous solution and the polymerization initiator) may be put into the organic solvent that is being stirred. The monomer composition (or the monomer aqueous solution and the polymerization initiator) may be put into the organic solvent that is left at rest.

Also in the batchwise reaction device 40, a hydrous gel produced by the above polymerization settles due to gravity. Due to gravity, the hydrous gel is naturally (automatically) supplied from the reactor 32 through the joint 36 to the discharge device 34. The hydrous gel that has reached the input port of the discharge device 34 is taken into the discharge device 34 together with the organic solvent. The function of the discharge device 34 is the same as the reaction device 14. The compressed hydrous gel is discharged through a discharge port 3.

By the discharge device 34, the hydrous gel can be extracted without moving the organic solvent from the interior of the reactor 42. After the hydrous gel is discharged from the discharge device 34, the next raw material liquid may be supplied. In addition, for example, by appropriately setting conditions such as the depth of the reactor 42, the temperature of the organic solvent and the like, it is also possible to supply the next raw material liquid such as the monomer aqueous solution and the organic solvent while the hydrous gel is being discharged from the discharge device 34. That is, the raw material liquid can be sequentially or continuously put into the reactor 42 with the organic solvent stored in the reactor 42. As described above, high productivity is achieved also in the batchwise reaction device 40 on the basis of the function of the discharge device 34. The raw material liquid means a liquid containing the monomer, and the concept thereof includes the monomer aqueous solution, the monomer composition, and a mixed liquid of these solutions and the organic solvent. Even in the process shown in FIG. 2, continuous operation is also possible.

In the method according to the present invention, unlike the conventional separation methods such as evaporation to dryness of an organic solvent and filtration of an organic solvent, there is an advantage in terms of energy, and the organic solvent, and the surfactant and the polymeric dispersing agent, which are used as necessary, are efficiently reused. Therefore, the method according to the present invention has advantages in that the cost is low, and the amount of the organic solvent remaining in the water-absorbent resin and the amounts of the surfactant and the polymeric dispersing agent remaining therein, which are used as necessary, can be reduced.

(Shape of Hydrous Gel)

In the present invention, the shape of the obtained hydrous gel is a spherical shape. The particle diameter of the hydrous gel (hereinafter, referred to as "gel particle diameter") is adjusted as appropriate in accordance with application of the obtained water-absorbent resin and the like.

The concept of the "spherical shape" includes shapes (e.g., a substantially spherical shape) other than a perfect spherical shape, and means that the ratio (also referred to as "sphericity") of the average long diameter and the average short diameter of the particles is preferably from 1.0 to 3.0. The average long diameter and the average short diameter of the particles are measured on the basis of an image taken by a microscope. The particles may have some dents, projections and depressions, and bubbles. In the present invention, the hydrous gel may be formed as an aggregate of micro spherical gels, or may be obtained as a mixture of micro spherical gels and an aggregate of the spherical gels.

In addition, when the hydrous gel is an aggregate of spherical gels, the particle diameter of each spherical gel forming the aggregate is referred to as primary particle diameter. In the present invention, from the viewpoint of being able to inhibit occurrence of micro powder in a drying step, the primary particle diameter is preferably 1 μm to 2000 μm, more preferably 10 μm to 1000 μm, and further preferably 50 μm to 800 μm. The primary particle diameter can be controlled on the basis of the polymerization conditions (flow rate, temperature, stirring speed, surfactant, etc.) and the diameters of droplets formed when the monomer composition is dispersed into the organic solvent.

(Solid Content Ratio of Hydrous Gel)

From the viewpoint of the cost for drying, the solid content ratio of the hydrous gel to be subjected to a drying step described later is preferably not less than 20% by mass, more preferably not less than 30% by mass, further preferably not less than 40% by mass, and particularly preferably not less than 45% by mass. In the separation method of the present invention, the residual liquid ratio can be reduced, and thus the solid content ratio of the hydrous gel can be increased. Regarding the upper limit, the solid content ratio of the hydrous gel is not greater than 90% by mass and preferably not greater than 80% by mass. The solid content ratio of the hydrous gel can be controlled on the basis of the concentration of the monomer component (the solid content of the monomer aqueous solution), the temperature during polymerization, partial drying performed as necessary after the polymerization, and the like. The method for calculating the solid content ratio of the hydrous gel will be described later.

(Residual Liquid Ratio of Hydrous Gel)

As described above, the residual liquid ratio of the hydrous gel discharged from the discharge device can be decreased by extrusion associated with compression. From the viewpoint of a load during drying and the cost for the organic solvent, the residual liquid ratio of the hydrous gel crosslinked polymer discharged from the discharge device is preferably not greater than 10% by mass, further preferably not greater than 9% by mass, and particularly preferably not greater than 8% by mass. However, in consideration of damage of the hydrous gel due to compression, the residual liquid ratio is preferably not less than 0.5% by mass and more preferably not less than 1% by mass. The residual liquid ratio (% by mass) is calculated by a method described below.

The residual liquid ratio is an index representing the amount of the organic solvent present between the particles of the hydrous gel separated from the organic solvent, and is calculated through the following procedure on the basis of the amount of the organic solvent that is used during polymerization of the water-absorbent resin and that is present between the gel particles of the discharged hydrous gel.

Specifically, the organic solvent present between the gel particles is extracted with ethyl acetate by immersing the hydrous gel separated from the organic solvent, into the ethyl acetate. The concentration of the organic solvent in the ethyl acetate is measured using gas chromatography. When the concentration of the organic solvent in the ethyl acetate is denoted by s (g/L), a residual liquid ratio R (% by mass) is obtained according to the following (formula 2).

$$R=100 \times s \times A/M \qquad \text{(formula 2)}$$

In (formula 2), M means the mass of the hydrous gel (g), and A means the volume of the ethyl acetate used for extraction (L).

(Reuse (Circulation) of Organic Solvent, Etc. After Separation)

In the present invention, the organic solvent separated in the separation step may be discarded or may be purified by distillation or the like and reused, but a part or all of the organic solvent is preferably reused in the polymerization step without being changed. In the case of reusing the organic solvent, the organic solvent is preferably circulated in the continuous reaction device as described above. The amount of the organic solvent to be reused, with respect to the amount of the organic solvent after the separation, is preferably not less than 50% by mass, more preferably not less than 70% by mass, and further preferably not less than 100% by mass. In addition, when the amount of the organic solvent has decreased due to evaporation or the like, the organic solvent can also be supplied as appropriate.

In the present invention, the organic solvent separated in the separation step may be circulated and reused in the case of continuous polymerization, and may be reused for the next batch, without being changed, in the case of batchwise polymerization.

[2-5] Other Post-Steps

The hydrous gel separated from the organic solvent in the separation step is subjected to a required step after the separation step. Specifically, the hydrous gel may be subjected to a drying step thereby to be made into a water-absorbent resin, and may be further subjected to steps such as a pulverization step, a classification step, a surface-crosslinking step, a granulation step, a sizing step, and the like thereby to be made into a water-absorbent resin.

Therefore, in addition to the respective steps described above, the method for producing the water-absorbent resin according to the present invention can include a drying step, a pulverization step, a classification step, a surface-crosslinking step, a sizing step, a fine powder removal step, a granulation step, and a fine powder reuse step according to need. In addition, the production method may further include a transport step, a storage step, a packing step, a keeping step, and the like.

(Drying Step)

This step is a step of drying the hydrous gel separated in the above separating step, to a desired solid content ratio to obtain a dried polymer in particle form. The hydrous gel may be subjected to the drying step after being adjusted to a desired particle diameter or particle size distribution by crushing or granulating the hydrous gel.

Examples of known methods for drying the hydrous gel include conductive heat transfer drying, convection heat transfer drying (hot air drying), drying under reduced pressure, infrared drying, microwave drying, drying through azeotropic dehydration with a hydrophobic organic solvent, ventilation drying, superheated steam drying using high-temperature steam, and the like. In consideration of drying efficiency and the like, the drying method can be selected from among these methods.

The drying temperature and the drying time are adjusted as appropriate with the solid content ratio of the obtained water-absorbent resin as an index. From the viewpoint of the water absorption performance of the water-absorbent resin, the solid content ratio is preferably not less than 85% by mass and more preferably 90% by mass to 98% by mass. The solid content ratio of the water-absorbent resin is a value calculated on the basis of a drying loss when a sample (water-absorbent resin) is dried at 180° C. for 3 hours. In the present invention, the dried polymer to be subjected to a surface-crosslinking step described later is referred to as "water-absorbent resin powder" for the sake of convenience.

(Pulverization Step and Classification Step)

The dried polymer in particle form obtained in the above drying step is made into water-absorbent resin powder having a controlled particle diameter or particle size distribution through a pulverization step and a classification step according to need.

In the pulverization step, a high-speed rotary type pulverizer such as a roll mill, a hammer mill, a screw mill, a pin mill, and the like, a vibration mill, a knuckle type pulverizer, a cylindrical mixer, or the like is selected as appropriate and used.

In the classification step, for example, sieve classification with a JIS standard sieve (JIS Z8801-1 (2000)), air-flow classification, or the like is selected as appropriate and used.

(Surface-Crosslinking Step)

The dried polymer in particle form obtained through the drying step, that is, the water-absorbent resin powder, is subjected to a surface-crosslinking step according to need. The surface-crosslinking step is a step of providing a portion having a high crosslinking density to a surface layer of the water-absorbent resin powder (a portion of several tens of micrometers from the surface of the water-absorbent resin powder). In the present invention, a known surface-crosslinking technique is used as appropriate.

(Sizing Step)

In the present application, the "sizing step" means a step of breaking the water-absorbent resin powder that loosely aggregates through the surface-crosslinking step, to adjust the particle diameter. The sizing step includes a fine powder removal step, a hydrous gel crushing step, and a classification step which are subsequent to the surface-crosslinking step.

(Fine Powder Reuse Step)

In the present application, the "fine powder reuse step" means a step of supplying fine powder to any step without changing the fine powder or after granulating the fine powder.

[3] Physical Properties of Water-Absorbent Resin

In the case where the water-absorbent resin obtained by the method according to the present invention is used for absorbent articles, particularly, for disposable diapers, among physical properties described below in (3-1) to (3-7), at least one, preferably two or more including AAP, more preferably three or more including AAP, further preferably four or more including AAP, particularly preferably five or more including AAP, and most preferably all the physical properties are desirably controlled within desired ranges. When all of the physical properties described below do not satisfy the ranges described below, the advantageous effects of the present invention are not sufficiently achieved, and sufficient performance may not be exerted particularly in so-called high-concentration disposable diapers in which the amount of the water-absorbent resin used per disposable diaper is large.

[3-1] CRC (Centrifuge Retention Capacity)

The CRC (centrifuge retention capacity) of the water-absorbent resin of the present invention is normally not less than 5 g/g, preferably not less than 15 g/g, and more preferably not less than 25 g/g. Regarding the upper limit thereof, a higher CRC is preferable. However, from the viewpoint of balance with the other physical properties, the CRC is preferably not greater than 70 g/g, more preferably not greater than 50 g/g, and further preferably not greater than 40 g/g.

When the above CRC is less than 5 g/g, the amount of absorption is small, and the water-absorbent resin is not suitable as an absorbent body for absorbent articles such as disposable diapers. In addition, when the above CRC exceeds 70 g/g, the speed at which body fluids such as urine, blood, and the like are absorbed decreases, and thus the water-absorbent resin is not suitable for use for high water absorption speed-type disposable diapers and the like. The CRC can be controlled by changing the types and the amounts of the internal crosslinking agent, a surface-crosslinking agent, and the like.

[3-2] AAP (Fluid Retention Capacity Under Load)

The AAP (fluid retention capacity under load) of the water-absorbent resin of the present invention is preferably not less than 20 g/g, more preferably not less than 22 g/g, further preferably not less than 23 g/g, particularly preferably not less than 24 g/g, and most preferably not less than 25 g/g. Regarding the upper limit thereof, the AAP is preferably not greater than 30 g/g. These AAPs are values measured with the load condition changed to 4.83 kPa (0.7 psi).

When the above AAP is less than 20 g/g, the amount of liquid return (sometimes referred to as "Re-Wet") when pressure is applied to the absorbent body increases, and thus the water-absorbent resin is not suitable as an absorbent body for absorbent articles such as disposable diapers. The AAP can be controlled by adjustment of the particle size, change of the surface-crosslinking agent, and the like.

[3-3] Ext (Water-Soluble Content)

The Ext (water-soluble content) of the water-absorbent resin of the present invention is normally not greater than 50% by mass, preferably not greater than 35% by mass, more preferably not greater than 25% by mass, and further preferably not greater than 15% by mass. The lower limit thereof is preferably 0% by mass and more preferably about 0.1% by mass. In the present invention, "about . . . " means that an error of ±5% is included.

When the above Ext exceeds 50% by mass, the water-absorbent resin may have low gel strength and inferior liquid permeability. Furthermore, since the Re-Wet increases, the water-absorbent resin is not suitable as an absorbent body for absorbent articles such as disposable diapers. The Ext can be controlled by changing the types and the amounts of the internal crosslinking agent and the like.

[3-4] Residual Monomer Amount

From the viewpoint of safety, the amount of the residual monomer contained in the water-absorbent resin according to the present invention is preferably not greater than 1000 ppm, more preferably not greater than 500 ppm, and further preferably not greater than 300 ppm. The lower limit thereof is preferably 0 ppm and more preferably about 10 ppm.

By making the residual monomer amount within the above range, a water-absorbent resin having alleviated stimulation to the skin of a human body and the like is obtained.

[3-5] Moisture Content

The moisture content of the water-absorbent resin according to the present invention preferably exceeds 0% by mass and is not greater than 20% by mass, more preferably in the range of 1% by mass to 15% by mass, further preferably in the range of 2% by mass to 13% by mass, and particularly preferably in the range of 2% by mass to 10% by mass.

By making the moisture content within the above range, a water-absorbent resin having excellent powder characteristics (e.g., fluidity, transportability, damage resistance, etc.) is obtained.

[3-6] Particle Size

The mass-average particle diameter (D50) of the water-absorbent resin of the present invention is preferably in the range of 200 µm to 700 µm, more preferably in the range of 250 µm to 600 µm, further preferably in the range of 250 µm to 500 µm, and particularly preferably in the range of 300 µm to 450 µm. In addition, the proportion of the particles having a particle diameter of less than 150 µm is preferably not greater than 20% by mass, more preferably not greater than 10% by mass, and further preferably not greater than 5% by mass. Moreover, the proportion of the particles having a particle diameter of not less than 850 µm is preferably not greater than 20% by mass, more preferably not greater than 15% by mass, and further preferably not greater than 10% by mass. In other words, the water-absorbent resin includes the particles having a particle diameter of less than 850 µm, in a proportion of preferably not less than 80% by mass, more preferably not less than 85% by mass, and further preferably not less than 90% by mass. The logarithmic standard deviation (σζ) of the particle size distribution is preferably in the range of 0.20 to 0.50, more preferably in the range of 0.25 to 0.40, and further preferably in the range of 0.27 to 0.35.

[3-7] Surface Tension

The surface tension of the water-absorbent resin of the present invention is preferably not less than 60 mN/m, more preferably not less than 65 mN/m, and further preferably not less than 70 mN/m. The upper limit thereof is normally 73 mN/m.

The surface tension that does not satisfy the above range brings that the amount of return (Re-Wet) in the case of use as an absorbent body for disposable diapers tends to increase, therefore that is not preferable. The surface tension can be controlled by selection of the types of the surfactant and the dispersing agent described above and the used amounts thereof. In addition, the preferable range of the surface tension is also applied to the hydrous gel separated from the organic solvent.

[4] Application of Water-Absorbent Resin

Preferable examples of application of the water-absorbent resin of the present invention include application as an absorbent body for absorbent articles such as disposable diapers, sanitary napkins, incontinence pads, and the like. In particular, the water-absorbent resin can be used as an absorbent body for high-concentration disposable diapers for which odor, coloring, and the like derived from the raw material have been problems. Furthermore, since the absorbent resin according to the present invention has excellent absorption time and a controlled particle size distribution, when the absorbent resin is used in an upper layer of the absorbent body, significant effects can be expected.

In addition, as the raw material of the absorbent body, an absorbent material such as pulp fibers and the like can be used together with the water-absorbent resin. In this case, the amount (core concentration) of the water-absorbent resin contained in the absorbent body is preferably in the range of 30% by mass to 100% by mass, more preferably in the range of 40% by mass to 100% by mass, further preferably in the range of 50% by mass to 100% by mass, even more preferably in the range of 60% by mass to 100% by mass, particularly preferably in the range of 70% by mass to 100% by mass, and most preferably in the range of 75% by mass to 95% by mass.

By making the core concentration within the above range, in the case where the absorbent body is used in an upper layer of an absorbent article, the absorbent article can be kept in a white state providing clean feel. Furthermore, the absorbent body is excellent in diffusion property with respect to body fluids such as urine, blood, and the like, and thus an increase in absorption amount can be expected due to efficient liquid distribution.

The present invention also includes embodiments described in the following items.

[Item 1]

A method for producing a water-absorbent resin comprising:

a polymerization step of polymerizing a monomer, which is a raw material of the water-absorbent resin, in a reactor to produce a hydrous gel crosslinked polymer in a solvent; and a separation step of separating and extracting the hydrous gel crosslinked polymer from the solvent, wherein in the separation step, a transfer-discharge device capable of transferring and discharging the hydrous gel crosslinked polymer is used, and the hydrous gel crosslinked polymer is extracted from the solvent while being compressed.

[Item 2]

The method according to Item 1, wherein the transfer-discharge device is directly connected to the reactor.

[Item 3]

The method according to Item 1 or 2, wherein a back pressure within the transfer-discharge device is not less than 0.1 MPa.

[Item 4]

The method according to any one of Items 1 to 3, wherein the hydrous gel crosslinked polymer extracted in the separation step has a residual liquid ratio of not greater than 10% by mass.

[Item 5]

The method according to any one of Items 1 to 4, wherein the transfer-discharge device includes a screw, and the screw has a compression ratio of not less than 1.5.

[Item 6]

A reaction device for polymerizing a monomer, which is a raw material of a water-absorbent resin, by liquid phase droplet polymerization to produce a hydrous gel crosslinked polymer, the reaction device comprising a transfer-discharge device capable of transferring and discharging the hydrous gel crosslinked polymer.

[Item 7]

The reaction device according to Item 6, wherein the transfer-discharge device has a gel compression mechanism that increases a degree of compression of the hydrous gel crosslinked polymer with progress of transfer.

[Item 8]

The reaction device according to Item 6 or 7, wherein a pressure adjustment mechanism capable of adjusting pressure applied to the hydrous gel crosslinked polymer is provided at a discharge port of the transfer-discharge device.

[Item 9]

A method for producing a water-absorbent resin by using the reaction device according to any one of Items 6 to 8.

[Item 10]

A discharge device for discharging a hydrous gel crosslinked polymer obtained by reverse phase suspension polymerization, from a slurry liquid containing the hydrous gel crosslinked polymer, the discharge device comprising:

at least one slurry liquid supply port and at least one hydrous gel crosslinked polymer discharge port, wherein when the slurry liquid moves from the slurry liquid supply port to the hydrous gel crosslinked polymer discharge port, pressure to the slurry liquid rises, separation between the hydrous gel crosslinked polymer and a dispersion medium progresses, the separated dispersion medium moves in a direction toward the slurry liquid supply port, and the hydrous gel crosslinked polymer is discharged through the hydrous gel crosslinked polymer discharge port.

[Item 11]

The discharge device according to Item 10, wherein a pressure adjustment mechanism capable of adjusting pressure applied to the hydrous gel crosslinked polymer is provided at the hydrous gel crosslinked polymer discharge port of the discharge device.

[Item 12]

The discharge device according to Item 10 or 11, wherein the slurry liquid supply port of the discharge device is connected to a product discharge port of a reactor in which continuous reverse phase suspension polymerization is carried out.

[Item 13]

A method for producing a water-absorbent resin by using the discharge device according to any one of Items 10 to 12.

EXAMPLES

The following will describe the present invention more specifically by means of Examples and Comparative Examples. However, the present invention is not limited to the description thereof, and an Example obtained by appropriately combining technical means that are disclosed in the respective Examples is also included in the technical scope of the present invention.

Unless specifically noted otherwise, a power source of 200 V or 100 V was used for electric apparatuses (including an apparatus for measuring physical properties of a hydrous gel) used in Examples and Comparative Examples. In addition, unless specifically noted otherwise, various physical properties of the hydrous gel were measured under conditions of room temperature (20 to 25° C.) and a relative humidity of 50% RH±10%.

Furthermore, for the sake of convenience, "liter" is sometimes represented as "l" or "L", and "% by mass" or "% by weight" is sometimes represented as "wt %".

[Methods for Measuring Physical Properties]

(a) Residual Liquid Ratio

The residual liquid ratio in the present invention is an index representing the amount of an organic solvent present between the particles of a hydrous gel separated from the organic solvent, and is calculated through the following procedure on the basis of the amount of the organic solvent that is used during polymerization of a water-absorbent resin and that is present between the gel particles of the discharged hydrous gel.

Specifically, the organic solvent present between the gel particles is extracted with ethyl acetate by immersing the hydrous gel separated from the organic solvent, into the ethyl acetate. The concentration of the organic solvent in the ethyl acetate is measured using gas chromatography. When the concentration of the organic solvent in the ethyl acetate is denoted by a (g/L), a residual liquid ratio R (% by mass) is obtained according to the following (formula 3).

$$R = 100 \times s \times A/M \quad \text{(formula 3)}$$

In (formula 3), M means the mass of the hydrous gel (g), and A means the volume of the ethyl acetate used for extraction (L).

A specific procedure for measuring the residual liquid ratio is described below.

(Creation of Calibration Curve)

An organic solvent used in Examples and Comparative Examples was added to ethyl acetate, and standard solutions of 40 g/L, 10 g/L, 5 g/L, 2 g/L, 0.5 g/L, and 0.1 g/L were prepared. Gas chromatography analysis was performed under the following conditions using these standard solutions, and a calibration curve of organic solvent concentration s and peak areas of obtained chromatograms was created.

(Calculation of Residual Liquid Ratio)

5.0 g of each of hydrous gels obtained in Examples and Comparative Examples was precisely weighed in a vial having a capacity of 100 ml, then 50 ml of ethyl acetate was added thereto, a stirrer chip was put thereinto, and the vial was immediately and hermetically sealed. Thereafter, the mixture was stirred at 300 rpm for 1 hour using a stirrer. After the stirring, the supernatant was passed through a 0.45-μm filter to obtain an organic solvent extract. Gas chromatography analysis was performed on the extract under the following conditions, the concentration s (g/L) of the organic solvent in the extract was obtained from the peak area of the obtained chromatogram and the calibration curve obtained above, and further a residual liquid ratio R (% by mass) was obtained according to (formula 3).

(Gas Chromatography Analysis Conditions)

Device: GC-2010 Plus, Auto Injector AOC-20i (manufactured by Shimadzu Corporation)

Column: SPB-5TM (low-polarity capillary column); length 30 m×inner diameter 0.53 mm, film thickness 0.5 μm Column temperature: 50° C.→150° C. (10° C./min, Hold; 5 min), total 15 min Vaporizing chamber: 200° C., split ratio; 20

Detector temperature: 200° C.

Detector: FID

Carrier gas: He, 36.2 cm/sec

Sample injection amount: 1 μL (b) Polymerization Ratio 1.00 g of a hydrous gel was put into 1000 g of ion-exchanged water, and the mixture was stirred at 300 rpm for 2 hours. Then, the mixture was filtrated to remove insoluble matter. The amount of the monomer extracted in the filtrate obtained by the above operation was measured by using liquid chromatography. When the amount of the monomer was used as a residual monomer amount m (g), a polymerization ratio C (% by mass) was obtained according to the following (formula 4).

$$C=100\times[1-m/\{(\alpha/100)\times(1-R/100)\times M\}]\quad\text{(formula 4)}$$

In (formula 4), M means the mass of the hydrous gel (g), R means the residual liquid ratio of the hydrous gel (% by mass), and α means the solid content ratio of the hydrous gel (% by mass). The solid content ratio is obtained by the following method.

(c) Solid Content Ratio of Hydrous Gel 2.00 g of a hydrous gel was put into an aluminum cup having a bottom surface with a diameter of 50 mm, and then the total mass W1 (g) of the sample (the hydrous gel and the aluminum cup) was accurately weighed. Next, the sample was left at rest within an oven whose atmospheric temperature was set to 180° C. After 24 hours elapsed, the sample was taken out of the oven, and the total mass W2 (g) was weighed with precision. When the mass of the hydrous gel subjected to this measurement was denoted by M (g), the solid content ratio α of the hydrous gel (% by mass) was obtained according to the following (formula 5).

$$\alpha=100-[\{(W1-W2)-M\times(R/100)\}/\{(1-R/100)\times M\}]\times 100\quad\text{(formula 5)}$$

In (formula 5), M means the mass of the hydrous gel (g), and R means the residual liquid ratio of the hydrous gel (% by mass).

(d) Surface Tension 50 ml of a physiological saline solution adjusted to 23° C.±2° C. was put into a sufficiently washed 100-ml beaker, and the surface tension of the physiological saline solution was measured by using a tensiometer (K11 automatic tensiometer, KRUSS GmbH). In this measurement, the value of surface tension needs to be within the range of 71 to 75 mN/m.

Next, a sufficiently washed stir bar having a length of 25 mm and coated with fluororesin and 0.5 g of a water-absorbent resin were put into a beaker containing the physiological saline solution, adjusted to 23° C.±2° C., whose surface tension had been measured, and the mixture was stirred at 500 rpm for 4 minutes. Thereafter, the stirring was stopped, the water-containing water-absorbent resin was settled, and then the surface tension of the supernatant (unit; mN/m) was measured. In the present invention, a plate method using a platinum plate was adopted, and prior to each measurement, the plate was sufficiently washed with deionized water and cleaned by heating with a gas burner before being used.

Example 1

A hydrous gel crosslinked polymer (hereinafter, referred to as "hydrous gel") (1) was prepared according to the process shown in FIG. 1, and then the obtained hydrous gel (1) was dried and further surface-crosslinked so as to produce spherical water-absorbent resin powder (1).

A static mixer (model: T3-15, manufactured by Noritake Co., Limited) was used as a mixing device, a two-fluid spray (external mixing type, nozzle inner diameter: 1.0 mm, auxiliary fluid: organic solvent, model: SETO07510PTFE, manufactured by H. IKEUCHI & CO., LTD.) was used as a supply device, a PFA tube (inner diameter: 25 mm, overall length: 10 m) vertically disposed was used as a reactor, and a screw extruder (pressure adjustment mechanism: multi-hole plate, hole diameter: 5.0 mm, hole area ratio: 26%) having a screw pitch decreasing when approaching a discharge port (see FIG. 3) was used as a discharge device. The discharge device was directly connected to a lower portion of the reactor and was structured to be capable of rough separation by gravity sedimentation (see the joint 36 and the discharge device 34 in FIG. 1).

As a preparation stage for polymerization reaction, n-heptane was put as an organic solvent into an auxiliary fluid flow passage of the two-fluid spray, the reactor, the discharge device, and pipes (including the joint) connecting these components. The position of the two-fluid spray was adjusted such that the tip end of the nozzle of the two-fluid spray was immersed in the organic solvent stored in the reactor.

Subsequently, the liquid-feeding pump was activated, and circulation of the organic solvent was initiated at a flow rate of 1000 ml/min. In this production method, the passage for the circulated organic solvent was branched into a passage for putting the organic solvent into the reactor through the two-fluid spray and a passage for directly putting the organic solvent into the reactor. The flow rate of the organic solvent put into the reactor through the two-fluid spray was set at 800 ml/min, and the flow rate of the organic solvent directly put into the reactor was set at 200 ml/min. Furthermore, a heat exchanger was activated, and the organic solvent was heated such that a set temperature was 85° C.

Next, acrylic acid, a 48.5% by mass sodium hydroxide aqueous solution and ion-exchanged water were mixed, and polyethylene glycol diacrylate (average degree of polymerization: 9) and trisodium diethylenetriamine pentaacetate were further blended into the mixture so as to prepare a monomer aqueous solution (1). The amount of oxygen dissolved in the monomer aqueous solution (1) was set to 1 ppm or less by blowing nitrogen gas into the monomer aqueous solution (1) while the temperature of the solution was kept at 25° C. In addition, separately, sodium persulfate and ion-exchanged water were mixed to prepare a 10% by mass sodium persulfate aqueous solution (1). Nitrogen substitution was performed by blowing nitrogen gas into the sodium persulfate aqueous solution (1).

Subsequently, the monomer aqueous solution (1) and the sodium persulfate aqueous solution (1) obtained by the above operation were individually supplied to the mixing device and mixed therein to prepare a monomer composition (1). A monomer concentration of the monomer composition (1) was 43% by mass, and the neutralization ratio of the monomer composition (1) was 70% by mole. In addition, the polyethylene glycol diacrylate, which is an internal cross-linking agent, was 0.02% by mole with respect to the monomer, trisodium diethylenetriamine pentaacetate, which is a chelating agent, was 100 ppm with respect to the monomer, and sodium persulfate, which is a polymerization initiator, was 0.1 g/mol with respect to the monomer.

Next, the monomer composition (1) prepared in the above mixing step was immediately sent to the monomer composition flow passage of the two-fluid spray. Thereafter, the monomer composition (1) was put into the organic solvent filling the reactor, at a flow rate of 40 ml/min (47.2 g/min) by using the above two-fluid spray. The monomer composition (1) was put inside such that the direction thereof agreed with the direction in which the organic solvent was circulated (parallel flow). In addition, the temperature of the monomer composition (1) before being put into the organic solvent was kept at 25° C.

The monomer composition (1) put inside by using the above two-fluid spray was dispersed in the organic solvent in droplet form (droplet diameter: 100 μm to 200 μm). The ratio of the monomer composition (1) and the organic solvent (W/O ratio) was 4.0% by volume.

The droplets formed with the monomer composition (1) turned into fine spherical gels while falling through the reactor filled with the organic solvent, as the polymerization reaction progressed. These fine spherical gels adhered to each other to form an aggregate while falling. Then, a hydrous gel (1) made of an aggregate of fine spherical gels having a diameter of 1 cm to 2 cm was confirmed near the discharge port of the reactor.

The hydrous gel (1) obtained by the above series of operations was continuously supplied from the reactor through the joint to the discharge device together with the organic solvent.

At the lower portion of the reactor (the joint), the hydrous gel (1) and the organic solvent were roughly separated from each other by gravity sedimentation. Due to the gravity sedimentation, the hydrous gel (1) reached the input port of the discharge device. Subsequently, the roughly separated hydrous gel (1) was squeezed by the screw of the discharge device and the multi-hole plate while being transferred, and was continuously discharged from the discharge device. The organic solvent separated in the discharge device was adjusted by the heat exchanger such that the set temperature was 85° C., and then was supplied to the reaction device again.

The obtained hydrous gel (1) obtained by the above operations had a shape obtained by fine spherical hydrous gels adhering and aggregating, and the primary particle diameter of the hydrous gel (1) was 210 μm. The conditions at the discharge device and the physical properties of the obtained hydrous gel (1) are shown in Table 1.

Example 2

A hydrous gel (2) was obtained by performing the same operations as in Example 1, except, in Example 1, a screw extruder having a reversely tapered shaft portion shape (pressure adjustment mechanism: multi-hole plate, hole diameter: 5.0 mm, hole area ratio: 26%) (see FIG. 4) was used as the discharge device. The conditions at the discharge device and the physical properties of the hydrous gel (2) are shown in Table 1.

Example 3

A hydrous gel (3) was obtained by performing the same operations as in Example 1, except, in Example 1, a screw extruder having a reversely tapered shaft portion shape and having a screw pitch decreasing when approaching a discharge port (pressure adjustment mechanism: multi-hole plate, hole diameter: 5.0 mm, hole area ratio: 26%) (see FIG. 5) was used as the discharge device. The conditions at the discharge device and the physical properties of the hydrous gel (3) are shown in Table 1.

Example 4

A hydrous gel (4) was obtained by performing the same operations as in Example 1, except, in Example 1, a screw extruder (screw shape: twin-single taper, pressure adjustment mechanism: multi-hole plate (holes with a diameter of 9.5 mm, hole area ratio: 48%)) (see FIG. 10) was used as the discharge device. The conditions at the discharge device and the physical properties of the hydrous gel (4) are shown in Table 1.

Example 5

A hydrous gel (5) was obtained by performing the same operations as in Example 4, except, in Example 4, a multi-hole plate having holes with a diameter of 9.5 mm was used and the hole area ratio thereof was changed to 41%. The conditions at the discharge device and the physical properties of the hydrous gel (5) are shown in Table 1.

Example 6

A hydrous gel (6) was obtained by performing the same operations as in Example 4, except, in Example 4, a multi-hole plate having holes with a diameter of 5.0 mm was used and the hole area ratio thereof was changed to 26%. The conditions at the discharge device and the physical properties of the hydrous gel (6) are shown in Table 1.

Example 7

A hydrous gel (7) was obtained by performing the same operations as in Example 4, except, in Example 4, a multi-hole plate having holes with a diameter of 3.1 mm was used and the hole area ratio thereof was changed to 37%. The conditions at the discharge device and the physical properties of the hydrous gel (7) are shown in Table 1.

Example 8

A hydrous gel (8) was obtained by performing the same operations as in Example 1, except, in Example 1, a screw extruder (screw shape: twin-single taper, pressure adjustment mechanism: air cylinder type back pressure plate) was used as the discharge device. The conditions at the discharge device and the physical properties of the hydrous gel (8) are shown in Table 1.

Example 9

A hydrous gel (9) was obtained by performing the same operations as in Example 8, except, in Example 8, the pressing force applied by the back pressure plate was adjusted and the back pressure at the discharge port of the discharge device (the pressure between the screw end and the air cylinder type back pressure plate) was changed to 1.0 MPa. The conditions at the discharge device and the physical properties of the hydrous gel (9) are shown in Table 1.

Example 10

A hydrous gel (10) was obtained by performing the same operations as in Example 8, except, in Example 8, the pressure adjustment mechanism was not installed. The conditions at the discharge device and the physical properties of the hydrous gel (10) are shown in Table 1.

Example 11

A hydrous gel (11) was obtained by performing the same operations as in Example 7, except, in Example 7, 0.005% by mass of a sucrose fatty acid eater (trade name: DK Ester F-50, DKS Co. Ltd.) was added as a dispersing agent to n-heptane.

The hydrous gel (11) obtained by the above operations had a shape obtained by fine spherical hydrous gels adhering and aggregating, and the primary particle diameter of the hydrous gel (11) was 100 µm. The conditions at the discharge device and the physical properties of the hydrous gel (11) are shown in Table 1.

Comparative Example 1

A comparative hydrous gel (1) was obtained by performing the same operations as in Example 1, except, in Example 1, a screw feeder (without a pressure adjustment mechanism) (see FIG. 11) was used as the discharge device. The conditions at the discharge device and the physical properties of the comparative hydrous gel (1) are shown in Table 1.

Comparative Example 2

A comparative hydrous gel (2) was obtained by performing the same operations as in Example 1, except, the organic solvent and the hydrous gel were extracted from the reaction device by using double valves instead of the discharge device in Example 1 and then the hydrous gel and the organic solvent were separated from each other by performing filtration with a gravity type filter. The conditions at the discharge device and the physical properties of the comparative hydrous gel (2) are shown in Table 1.

Although not shown in Table 1, when the surface tension of the water-absorbent resin obtained after drying was measured for the hydrous gels (1) to (11) obtained in Examples 1 to 11, the surface tension was about 72 mN/m in Examples 1 to 10 and was 71 mN/m in Example 11.

[Table 1]

TABLE 1

Specifications and Evaluation Results of Examples and Comparative Examples

| | Screw shape | Compression ratio | Pressure adjustment device | Hole diameter [mm] | Hole area ratio [%] | Back pressure [MPa] | Hydrous gel Residual liquid ratio [wt %] |
|---|---|---|---|---|---|---|---|
| Example 1 | Pitch large - small | 5 | Multi-hole plate | 5.0 | 26 | 0.5 | 3.1 |
| Example 2 | Reverse taper | 2 | Multi-hole plate | 5.0 | 26 | 0.2 | 7.0 |
| Example 3 | Reverse taper + pitch large - small | 10 | Multi-hole plate | 5.0 | 26 | 0.6 | 2.5 |
| Example 4 | Twin-single taper | 38 | Multi-hole plate | 9.5 | 48 | 0.3 | 4.1 |
| Example 5 | Twin-single taper | 38 | Multi-hole plate | 9.5 | 41 | 0.4 | 2.9 |
| Example 6 | Twin-single taper | 38 | Multi-hole plate | 5.0 | 26 | 0.7 | 1.9 |
| Example 7 | Twin-single taper | 38 | Multi-hole plate | 3.1 | 37 | 0.9 | 1.7 |
| Example 8 | Twin-single taper | 38 | Air cylinder type back pressure plate | — | — | 0.5 | 2.5 |
| Example 9 | Twin-single taper | 38 | Air cylinder type back pressure plate | — | — | 1.0 | 1.5 |
| Example 10 | Twin-single taper | 38 | None | — | — | 0.0 | 7.9 |

TABLE 1-continued

Specifications and Evaluation Results of Examples and Comparative Examples

| | Screw shape | Compression ratio | Pressure adjustment device | Hole diameter [mm] | Hole area ratio [%] | Back pressure [MPa] | Hydrous gel Residual liquid ratio [wt %] |
|---|---|---|---|---|---|---|---|
| Example 11 | Twin-single taper | 38 | Multi-hole plate | 3.1 | 37 | 0.6 | 2.0 |
| Comparative Example 1 | Screw feeder | 1 | None | — | — | 0.0 | 100 |
| Comparative Example 2 | Filtration with gravity type filter (150 μm) | | | — | — | — | 28 |

As shown in Table 1 above, whereas the residual liquid ratios of the hydrous gels in Examples 1 to 11 are 1.5% by mass to 7.9% by mass, the residual liquid ratios of the hydrous gels in Comparative Examples 1 and 2 are 28% by mass and 100% by mass and very high. Thus, advantages of the present invention are clear. In the present invention, a hydrous gel having a low residual liquid ratio can be efficiently extracted. With the method for producing the water-absorbent resin, the organic solvent and the expensive surfactant, which is used as necessary, can be efficiently separated from the water-absorbent resin and further can be reused, and thus a water-absorbent resin having improved physical properties can be efficiently produced at low cost.

INDUSTRIAL APPLICABILITY

The water-absorbent resin obtained by the present invention is suitable for application as an absorbent body for sanitary articles such as disposable diapers.

DESCRIPTION OF THE REFERENCE CHARACTERS

10 . . . mixing device
12 . . . supply device
14 . . . reaction device
16 . . . heat exchanger
18 . . . liquid-feeding pump
1, 2, 20, 22, 30 . . . pipe
3 . . . discharge port
32, 42 . . . reactor
34, 50, 70, 90, 110, 130, 150, 170, 200, 220 . . . discharge device (transfer-discharge device)
36 . . . joint
51, 71, 91, 111, 131, 151, 221 . . . pitch
53, 73, 93, 113, 133, 153, 173, 223 . . . groove
54, 74, 94, 114, 134, 154, 174, 175, 202, 204, 224 . . . screw
55, 75, 95, 115, 135, 155, 177 . . . clearance

The invention claimed is:

1. A method for producing a water-absorbent resin comprising:
a polymerization step of polymerizing a monomer, which is a raw material of the water-absorbent resin, to obtain a hydrous gel crosslinked polymer dispersed in an organic solvent; and
a separation step of separating the organic solvent and the hydrous gel crosslinked polymer from each other, wherein
the separation step includes transfer, compression, and discharge of the hydrous gel crosslinked polymer by a discharge device having an input port receiving said hydrous gel crosslinked polymer dispersed in the organic solvent and a discharge port for discharging the hydrous gel crosslinked polymer, wherein the hydrous gel crosslinked polymer is transferred from the input port to the discharge port, and the organic solvent is transferred in a direction opposite a direction of transfer of the hydrous gel crosslinked polymer from the discharge port toward the input port, and the hydrous gel crosslinked polymer discharged in the separation step has a residual liquid ratio of not greater than 10% by mass.

2. The method according to claim 1, wherein, in the separation step, the hydrous gel crosslinked polymer is squeezed while being transferred.

3. The method according to claim 1, wherein the compression in the separation step is to apply a pressure of not less than 0.1 MPa to the hydrous gel crosslinked polymer.

4. The method according to claim 1, wherein, in the separation step, a screw extruder including a screw having a compression ratio of not less than 1.5 is used.

5. The method according to claim 1, wherein the organic solvent contains a surfactant and/or a polymeric dispersing agent.

6. The method according to claim 1, wherein the organic solvent separated in the separation step is reused in the polymerization step.

7. The method according to claim 1, wherein a reaction device is used in the polymerization step of obtaining the hydrous gel crosslinked polymer and in the separation step of separating the organic solvent and the hydrous gel crosslinked polymer from each other, and where said reaction device comprises the discharge device capable of transferring, compressing and discharging the hydrous gel crosslinked polymer.

8. The method of claim 1, further comprising adjusting a pressure applied to the hydrous gel crosslinked polymer at the discharge port of the discharge device by an adjustment mechanism.

9. The method of claim 1, wherein the residual liquid ratio of the hydrous gel crosslinked polymer is not less than 0.5% by mass and not greater than 10% by mass.

10. The method of claim 1, wherein the residual liquid ratio is calculated according to the following formula after extracting the organic solvent in the hydrous gel crosslinked polymer with ethyl acetate and measuring the concentration of the organic solvent in ethyl acetate by gas chromatography:

$$R = 100 \times s \times A/M$$

wherein R is the residual liquid ratio (% by mass), s is the concentration of the organic solvent in the ethyl acetate (g/L), M is the mass of the hydrous gel (g) and A is the volume of the ethyl acetate used for extraction (L).

11. The method of claim 1, wherein a solid content ratio of the hydrous gel crosslinked polymer discharged in the separation step is not less than 20% by mass and not greater than 80% by mass.

12. The method of claim 1, wherein a ratio W/O of a volume W of a monomer composition containing the monomer as a main component to a volume O of the organic solvent is 1% by volume to 40% by volume.

* * * * *